(12) United States Patent
Kamath et al.

(10) Patent No.: US 9,446,194 B2
(45) Date of Patent: Sep. 20, 2016

(54) METHODS AND SYSTEMS FOR PROMOTING GLUCOSE MANAGEMENT

(75) Inventors: Apurv Ullas Kamath, San Diego, CA (US); Jack Pryor, San Diego, CA (US); Alexandra Lynn Carlton, San Diego, CA (US); Kristin Koenekamp Cote, Oakland, CA (US); Leif Bowman, Livermore, CA (US); Michael Robert Mensinger, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1656 days.

(21) Appl. No.: 12/748,069

(22) Filed: Mar. 26, 2010

(65) Prior Publication Data

US 2010/0261987 A1  Oct. 14, 2010

Related U.S. Application Data

(60) Provisional application No. 61/164,326, filed on Mar. 27, 2009.

(51) Int. Cl.
*A61B 5/00* (2006.01)
*A61M 5/172* (2006.01)
(Continued)

(52) U.S. Cl.
CPC .......... *A61M 5/1723* (2013.01); *A61B 5/0004* (2013.01); *A61B 5/1495* (2013.01); *A61B 5/14532* (2013.01); *A61B 5/14546* (2013.01); *A61B 5/4833* (2013.01); *A61B 5/725* (2013.01); *A61B 5/743* (2013.01); *A61B 5/744* (2013.01);
(Continued)

(58) Field of Classification Search
CPC .. A61B 5/14532; A61B 5/744; A61B 5/725; A61B 5/1495; A61B 5/746; A61B 5/7475; A61B 5/14546; A61B 5/0004; A61B 5/743; A61B 5/4833; G06F 19/3418; G06F 19/3406; G06F 19/3437
USPC .......................... 600/365, 345, 347, 316, 319
See application file for complete search history.

(56) References Cited

U.S. PATENT DOCUMENTS 3,210,578 A   10/1965   Sherer
3,219,533 A   11/1965   Mullins
(Continued)

FOREIGN PATENT DOCUMENTS

EP   0 098 592   1/1984
EP   0 127 958   12/1984
(Continued)

OTHER PUBLICATIONS

US 7,530,950, 5/2009, Brister et al. (withdrawn).
(Continued)

*Primary Examiner* — Michael Kahelin
*Assistant Examiner* — Tho Tran
(74) *Attorney, Agent, or Firm* — Knobbe Martens Olson & Bear, LLP

(57) ABSTRACT

Methods and systems for encouraging interactions with a glucose monitoring system include incrementing a score and/or providing a reward based on a variety of different interactions with the glucose monitoring system. The interactions which improve the score may include initiating or changing displays, downloading data, setting operational parameters and other interactions that are independent of a user's glucose measurements. Encouraging these interactions can enhance success in maintaining healthy glucose concentrations.

4 Claims, 16 Drawing Sheets

(51) Int. Cl.
*A61B 5/145* (2006.01)
*G06F 19/00* (2011.01)
*A61B 5/1495* (2006.01)
*A61M 5/142* (2006.01)

(52) U.S. Cl.
CPC ............ *A61B 5/746* (2013.01); *A61B 5/7475* (2013.01); *A61M 5/142* (2013.01); *G06F 19/3406* (2013.01); *G06F 19/3418* (2013.01); *A61M 2205/3303* (2013.01); *A61M 2205/502* (2013.01); *A61M 2205/581* (2013.01); *A61M 2205/582* (2013.01); *A61M 2205/583* (2013.01); *A61M 2230/06* (2013.01); *A61M 2230/201* (2013.01); *A61M 2230/63* (2013.01); *G06F 19/3437* (2013.01); *G06F 19/3468* (2013.01)

(56) References Cited

U.S. PATENT DOCUMENTS

| | | |
|---|---|---|
| 3,780,727 A | 12/1973 | King |
| 3,898,984 A | 8/1975 | Mandel et al. |
| 3,929,971 A | 12/1975 | Roy |
| 3,943,918 A | 3/1976 | Lewis |
| 3,979,274 A | 9/1976 | Newman |
| 4,076,656 A | 2/1978 | White et al. |
| 4,240,889 A | 12/1980 | Yoda et al. |
| 4,253,469 A | 3/1981 | Aslan |
| 4,403,984 A | 9/1983 | Ash et al. |
| 4,415,666 A | 11/1983 | D'Orazio et al. |
| 4,431,004 A | 2/1984 | Bessman et al. |
| 4,436,094 A | 3/1984 | Cerami |
| 4,454,295 A | 6/1984 | Wittmann et al. |
| 4,494,950 A | 1/1985 | Fischell |
| 4,506,680 A | 3/1985 | Stokes |
| RE31,916 E | 6/1985 | Oswin et al. |
| 4,554,927 A | 11/1985 | Fussell |
| 4,577,642 A | 3/1986 | Stokes |
| RE32,361 E | 2/1987 | Duggan |
| 4,655,880 A | 4/1987 | Liu |
| 4,671,288 A | 6/1987 | Gough |
| 4,680,268 A | 7/1987 | Clark, Jr. |
| 4,703,756 A | 11/1987 | Gough et al. |
| 4,711,251 A | 12/1987 | Stokes |
| 4,721,677 A | 1/1988 | Clark |
| 4,731,726 A | 3/1988 | Allen |
| 4,757,022 A | 7/1988 | Shults et al. |
| 4,759,828 A | 7/1988 | Young et al. |
| 4,781,798 A | 11/1988 | Gough |
| 4,805,625 A | 2/1989 | Wyler |
| 4,849,458 A | 7/1989 | Reed et al. |
| 4,852,573 A | 8/1989 | Kennedy |
| 4,858,615 A | 8/1989 | Meinema |
| 4,883,057 A | 11/1989 | Broderick |
| 4,890,620 A | 1/1990 | Gough |
| 4,890,621 A | 1/1990 | Hakky |
| 4,919,141 A | 4/1990 | Zier et al. |
| 4,927,516 A | 5/1990 | Yamaguchi et al. |
| 4,944,299 A | 7/1990 | Silvian |
| 4,953,552 A | 9/1990 | DeMarzo |
| 4,975,636 A | 12/1990 | Desautels |
| 4,986,671 A | 1/1991 | Sun et al. |
| 4,988,341 A | 1/1991 | Columbus et al. |
| 4,994,167 A | 2/1991 | Shults et al. |
| 5,002,572 A | 3/1991 | Picha |
| 5,030,333 A | 7/1991 | Clark, Jr. |
| 5,050,612 A | 9/1991 | Matsumura |
| 5,068,536 A | 11/1991 | Rosenthal |
| 5,077,476 A | 12/1991 | Rosenthal |
| 5,097,834 A | 3/1992 | Skrabal |
| 5,101,814 A | 4/1992 | Palti |
| 5,108,819 A | 4/1992 | Heller et al. |
| 5,137,028 A | 8/1992 | Nishimura |
| 5,140,985 A | 8/1992 | Schroeder et al. |
| 5,160,418 A | 11/1992 | Mullen |
| 5,165,407 A | 11/1992 | Wilson et al. |
| 5,190,041 A | 3/1993 | Palti |
| 5,198,771 A | 3/1993 | Fidler et al. |
| 5,208,147 A | 5/1993 | Kagenow et al. |
| 5,243,983 A | 9/1993 | Tarr et al. |
| 5,264,104 A | 11/1993 | Gregg et al. |
| 5,266,179 A | 11/1993 | Nankai et al. |
| 5,269,891 A | 12/1993 | Colin |
| 5,282,848 A | 2/1994 | Schmitt |
| 5,287,753 A | 2/1994 | Routh et al. |
| 5,299,571 A | 4/1994 | Mastrototaro |
| 5,307,263 A | 4/1994 | Brown |
| 5,316,008 A | 5/1994 | Suga et al. |
| 5,324,322 A | 6/1994 | Grill et al. |
| 5,330,634 A | 7/1994 | Wong et al. |
| 5,331,555 A | 7/1994 | Hashimoto et al. |
| 5,337,747 A | 8/1994 | Neftel |
| 5,368,224 A | 11/1994 | Richardson et al. |
| 5,372,133 A | 12/1994 | Hogen Esch |
| 5,376,070 A | 12/1994 | Purvis et al. |
| 5,390,671 A | 2/1995 | Lord et al. |
| 5,391,250 A | 2/1995 | Cheney, II et al. |
| 5,411,866 A | 5/1995 | Luong |
| 5,429,735 A | 7/1995 | Johnson et al. |
| 5,431,160 A | 7/1995 | Wilkins |
| 5,434,412 A | 7/1995 | Sodickson et al. |
| 5,462,051 A | 10/1995 | Oka et al. |
| 5,462,064 A | 10/1995 | D'Angelo et al. |
| 5,474,552 A | 12/1995 | Palti |
| 5,494,562 A | 2/1996 | Maley et al. |
| 5,497,772 A | 3/1996 | Schulman et al. |
| 5,502,396 A | 3/1996 | Desarzens et al. |
| 5,507,288 A | 4/1996 | Bocker et al. |
| 5,513,636 A | 5/1996 | Palti |
| 5,518,601 A | 5/1996 | Foos et al. |
| 5,531,878 A | 7/1996 | Vadgama et al. |
| 5,540,828 A | 7/1996 | Yacynych |
| 5,553,616 A | 9/1996 | Ham et al. |
| 5,568,806 A | 10/1996 | Cheney, II et al. |
| 5,569,186 A | 10/1996 | Lord et al. |
| 5,582,184 A | 12/1996 | Ericson et al. |
| 5,584,813 A | 12/1996 | Livingston et al. |
| 5,586,553 A | 12/1996 | Halili et al. |
| 5,653,863 A | 8/1997 | Genshaw et al. |
| 5,660,163 A | 8/1997 | Schulman et al. |
| 5,678,571 A * | 10/1997 | Brown .......................... 128/898 |
| 5,695,623 A | 12/1997 | Michel et al. |
| 5,711,861 A | 1/1998 | Ward et al. |
| 5,730,654 A | 3/1998 | Brown |
| 5,743,262 A | 4/1998 | Lepper, Jr. et al. |
| 5,749,907 A | 5/1998 | Mann |
| 5,781,455 A | 7/1998 | Hyodo et al. |
| 5,791,344 A | 8/1998 | Schulman et al. |
| 5,795,774 A | 8/1998 | Matsumoto et al. |
| 5,800,420 A | 9/1998 | Gross |
| 5,806,517 A | 9/1998 | Gerhardt et al. |
| 5,807,375 A | 9/1998 | Gross et al. |
| 5,814,599 A | 9/1998 | Mitragotri et al. |
| 5,822,715 A | 10/1998 | Worthington et al. |
| 5,836,887 A | 11/1998 | Oka et al. |
| 5,836,989 A | 11/1998 | Shelton |
| 5,861,019 A | 1/1999 | Sun et al. |
| 5,871,514 A | 2/1999 | Wiklund et al. |
| 5,882,494 A | 3/1999 | Van Antwerp |
| 5,897,578 A | 4/1999 | Wiklund et al. |
| 5,899,855 A | 5/1999 | Brown |
| 5,904,708 A | 5/1999 | Goedeke |
| 5,913,998 A | 6/1999 | Butler et al. |
| 5,914,026 A | 6/1999 | Blubaugh, Jr. et al. |
| 5,919,215 A | 7/1999 | Wiklund et al. |
| 5,931,814 A | 8/1999 | Alex et al. |
| 5,933,136 A | 8/1999 | Brown |
| 5,944,661 A | 8/1999 | Swette et al. |
| 5,957,854 A | 9/1999 | Besson et al. |
| 5,961,451 A | 10/1999 | Reber et al. |
| 5,964,993 A | 10/1999 | Blubaugh et al. |
| 5,965,380 A | 10/1999 | Heller et al. |
| 5,971,922 A | 10/1999 | Arita et al. |

(56) References Cited

U.S. PATENT DOCUMENTS

| | | | |
|---|---|---|---|
| 5,976,085 A | 11/1999 | Kimball et al. |
| 5,995,860 A | 11/1999 | Sun et al. |
| 6,001,067 A | 12/1999 | Shults et al. |
| 6,016,448 A | 1/2000 | Busacker et al. |
| 6,024,699 A | 2/2000 | Surwit et al. |
| 6,027,445 A | 2/2000 | Von Bahr |
| 6,036,924 A | 3/2000 | Simons et al. |
| 6,049,727 A | 4/2000 | Crothall |
| 6,059,946 A | 5/2000 | Yukawa et al. |
| 6,081,735 A | 6/2000 | Diab et al. |
| 6,081,736 A | 6/2000 | Colvin et al. |
| 6,083,523 A | 7/2000 | Dionne et al. |
| 6,088,608 A | 7/2000 | Schulman et al. |
| 6,091,975 A | 7/2000 | Daddona et al. |
| 6,093,172 A | 7/2000 | Funderburk et al. |
| 6,107,083 A | 8/2000 | Collins et al. |
| 6,122,536 A | 9/2000 | Sun et al. |
| 6,123,827 A | 9/2000 | Wong et al. |
| 6,135,978 A | 10/2000 | Houben et al. |
| 6,144,869 A | 11/2000 | Berner et al. |
| 6,162,611 A | 12/2000 | Heller et al. |
| 6,168,568 B1 | 1/2001 | Gavriely |
| 6,175,752 B1 * | 1/2001 | Say et al. ................ 600/345 |
| 6,180,416 B1 | 1/2001 | Kurnik et al. |
| 6,201,980 B1 | 3/2001 | Darrow et al. |
| 6,201,993 B1 | 3/2001 | Kruse et al. |
| 6,208,894 B1 | 3/2001 | Schulman et al. |
| 6,212,416 B1 | 4/2001 | Ward et al. |
| 6,212,424 B1 | 4/2001 | Robinson |
| 6,223,083 B1 | 4/2001 | Rosar |
| 6,230,059 B1 | 5/2001 | Duffin |
| 6,233,080 B1 | 5/2001 | Brenner et al. |
| 6,233,471 B1 | 5/2001 | Berner et al. |
| 6,248,067 B1 | 6/2001 | Causey, III et al. |
| 6,256,522 B1 | 7/2001 | Schultz |
| 6,259,937 B1 | 7/2001 | Schulman et al. |
| 6,272,364 B1 | 8/2001 | Kurnik |
| 6,272,480 B1 | 8/2001 | Tresp et al. |
| 6,275,717 B1 | 8/2001 | Gross et al. |
| 6,284,478 B1 | 9/2001 | Heller et al. |
| 6,299,578 B1 | 10/2001 | Kurnik et al. |
| 6,302,855 B1 | 10/2001 | Lav et al. |
| 6,309,351 B1 | 10/2001 | Kurnik et al. |
| 6,309,884 B1 | 10/2001 | Cooper et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,366,794 B1 | 4/2002 | Moussy et al. |
| 6,370,941 B2 | 4/2002 | Nakamura |
| 6,379,301 B1 | 4/2002 | Worthington et al. |
| 6,416,651 B1 | 7/2002 | Millar |
| 6,424,847 B1 | 7/2002 | Mastrototaro et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,484,046 B1 | 11/2002 | Say et al. |
| 6,510,329 B2 | 1/2003 | Heckel |
| 6,512,939 B1 | 1/2003 | Colvin et al. |
| 6,526,298 B1 | 2/2003 | Khalil et al. |
| 6,527,729 B2 | 3/2003 | Turcott |
| 6,544,212 B2 | 4/2003 | Galley et al. |
| 6,546,268 B1 | 4/2003 | Ishikawa et al. |
| 6,546,269 B1 | 4/2003 | Kurnik |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,558,320 B1 | 5/2003 | Causey et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,579,498 B1 | 6/2003 | Eglise |
| 6,579,690 B1 | 6/2003 | Bonnecaze et al. |
| 6,585,519 B1 * | 7/2003 | Jenkins et al. ................ 434/236 |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,072 B2 | 8/2003 | Struys et al. |
| 6,618,934 B1 | 9/2003 | Feldman et al. |
| 6,633,772 B2 | 10/2003 | Ford et al. |
| 6,641,533 B2 | 11/2003 | Causey et al. |
| 6,673,022 B1 | 1/2004 | Bobo et al. |
| 6,673,596 B1 | 1/2004 | Sayler et al. |
| 6,699,188 B2 | 3/2004 | Wessel |
| 6,702,857 B2 | 3/2004 | Brauker et al. |
| 6,702,972 B1 | 3/2004 | Markle |
| 6,741,877 B1 | 5/2004 | Shults et al. |
| 6,869,413 B2 | 3/2005 | Langley et al. |
| 6,895,263 B2 | 5/2005 | Shin et al. |
| 6,925,393 B1 | 8/2005 | Kalatz et al. |
| 6,931,327 B2 | 8/2005 | Goode et al. |
| 6,952,604 B2 | 10/2005 | DeNuzzio et al. |
| 6,998,247 B2 | 2/2006 | Monfre et al. |
| 7,011,630 B2 | 3/2006 | Desai et al. |
| 7,025,743 B2 | 4/2006 | Mann et al. |
| 7,029,444 B2 | 4/2006 | Shin et al. |
| 7,060,059 B2 | 6/2006 | Keith et al. |
| 7,074,307 B2 | 7/2006 | Simpson et al. |
| 7,098,803 B2 | 8/2006 | Mann et al. |
| 7,134,999 B2 | 11/2006 | Brauker et al. |
| 7,169,289 B2 | 1/2007 | Schulein et al. |
| 7,229,288 B2 | 6/2007 | Stuart et al. |
| 7,261,690 B2 | 8/2007 | Teller et al. |
| 7,261,691 B1 * | 8/2007 | Asomani ................ 600/300 |
| 7,267,665 B2 | 9/2007 | Steil et al. |
| 7,276,029 B2 | 10/2007 | Goode et al. |
| 7,278,983 B2 | 10/2007 | Ireland et al. |
| 7,295,867 B2 | 11/2007 | Berner et al. |
| 7,354,420 B2 | 4/2008 | Steil et al. |
| 7,359,723 B2 | 4/2008 | Jones |
| 7,402,153 B2 | 7/2008 | Steil et al. |
| 7,417,164 B2 | 8/2008 | Suri |
| 7,426,408 B2 | 9/2008 | DeNuzzio et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,618,368 B2 | 11/2009 | Brown |
| 7,624,028 B1 | 11/2009 | Brown |
| 7,640,032 B2 | 12/2009 | Jones |
| 7,640,048 B2 | 12/2009 | Dobbles et al. |
| 2001/0016682 A1 | 8/2001 | Berner et al. |
| 2001/0041830 A1 | 11/2001 | Varalli et al. |
| 2001/0051768 A1 | 12/2001 | Schulman et al. |
| 2002/0019022 A1 | 2/2002 | Dunn et al. |
| 2002/0026111 A1 | 2/2002 | Ackerman |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0065453 A1 | 5/2002 | Lesho et al. |
| 2002/0068860 A1 | 6/2002 | Clark, Jr. |
| 2002/0099282 A1 | 7/2002 | Knobbe et al. |
| 2002/0111547 A1 | 8/2002 | Knobbe et al. |
| 2002/0119711 A1 | 8/2002 | Van Antwerp et al. |
| 2002/0155615 A1 | 10/2002 | Novikov et al. |
| 2002/0161288 A1 | 10/2002 | Shin et al. |
| 2002/0198513 A1 | 12/2002 | Lebel et al. |
| 2003/0006669 A1 | 1/2003 | Pei et al. |
| 2003/0023171 A1 | 1/2003 | Sato et al. |
| 2003/0023317 A1 | 1/2003 | Brauker et al. |
| 2003/0028089 A1 | 2/2003 | Galley et al. |

(56) References Cited

U.S. PATENT DOCUMENTS

| | | |
|---|---|---|
| 2003/0032874 A1 | 2/2003 | Rhodes et al. |
| 2003/0050537 A1* | 3/2003 | Wessel .................. 600/300 |
| 2003/0050546 A1 | 3/2003 | Desai et al. |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100821 A1 | 5/2003 | Heller et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0187338 A1 | 10/2003 | Say et al. |
| 2003/0188427 A1 | 10/2003 | Say et al. |
| 2003/0211625 A1 | 11/2003 | Cohan |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0235817 A1 | 12/2003 | Bartkowiak et al. |
| 2004/0011671 A1 | 1/2004 | Shults et al. |
| 2004/0015063 A1 | 1/2004 | DeNuzzio et al. |
| 2004/0024327 A1 | 2/2004 | Brodnick |
| 2004/0039298 A1 | 2/2004 | Abreu |
| 2004/0045879 A1 | 3/2004 | Shults et al. |
| 2004/0078219 A1 | 4/2004 | Kaylor |
| 2004/0106857 A1 | 6/2004 | Gough |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0167801 A1 | 8/2004 | Say et al. |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2005/0010265 A1 | 1/2005 | Baru Fassio et al. |
| 2005/0010442 A1* | 1/2005 | Kragh ................ 705/2 |
| 2005/0021372 A1 | 1/2005 | Mikkelsen et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027463 A1 | 2/2005 | Goode et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 | 5/2005 | DeNuzzio et al. |
| 2005/0101847 A1 | 5/2005 | Routt et al. |
| 2005/0113653 A1 | 5/2005 | Fox et al. |
| 2005/0115832 A1 | 6/2005 | Simpson et al. |
| 2005/0121322 A1 | 6/2005 | Say |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0187720 A1 | 8/2005 | Goode et al. |
| 2005/0192557 A1 | 9/2005 | Brauker et al. |
| 2005/0203360 A1 | 9/2005 | Brauker et al. |
| 2005/0211571 A1 | 9/2005 | Schulein et al. |
| 2005/0215872 A1 | 9/2005 | Berner et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0089542 A1 | 4/2006 | Sands |
| 2006/0100588 A1 | 5/2006 | Brunnberg et al. |
| 2006/0183984 A1 | 8/2006 | Dobbles et al. |
| 2006/0183985 A1 | 8/2006 | Brister et al. |
| 2006/0222566 A1 | 10/2006 | Brauker et al. |
| 2006/0258929 A1 | 11/2006 | Goode et al. |
| 2007/0010950 A1* | 1/2007 | Abensour .......... A61B 5/14532 702/19 |
| 2007/0016381 A1 | 1/2007 | Kamath et al. |
| 2007/0032706 A1 | 2/2007 | Kamath et al. |
| 2007/0049873 A1 | 3/2007 | Hansen et al. |
| 2007/0066873 A1 | 3/2007 | Kamath et al. |
| 2007/0179356 A1* | 8/2007 | Wessel .................. 600/300 |
| 2007/0203410 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0288266 A1* | 12/2007 | Sysko .................. G06Q 10/00 705/2 |
| 2008/0015422 A1 | 1/2008 | Wessel |
| 2008/0021666 A1 | 1/2008 | Goode et al. |
| 2008/0033254 A1 | 2/2008 | Kamath et al. |
| 2008/0183061 A1 | 7/2008 | Goode et al. |
| 2008/0183399 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0189051 A1 | 8/2008 | Goode et al. |
| 2008/0194936 A1 | 8/2008 | Goode et al. |
| 2008/0194937 A1 | 8/2008 | Goode et al. |
| 2008/0195967 A1 | 8/2008 | Goode et al. |
| 2008/0215003 A1* | 9/2008 | Kornerup et al. ............ 604/116 |
| 2008/0249384 A1* | 10/2008 | Skyggebjerg et al. ....... 600/347 |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0305009 A1 | 12/2008 | Gamsey et al. |
| 2008/0305506 A1 | 12/2008 | Suri |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018418 A1 | 1/2009 | Markle et al. |
| 2009/0018426 A1 | 1/2009 | Markle et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0058635 A1* | 3/2009 | LaLonde ............ A61N 1/37282 340/539.11 |
| 2009/0061528 A1 | 3/2009 | Suri |
| 2009/0062635 A1 | 3/2009 | Brauker et al. |
| 2009/0076361 A1 | 3/2009 | Kamath et al. |
| 2009/0081803 A1 | 3/2009 | Gamsey et al. |
| 2009/0124877 A1 | 5/2009 | Goode, Jr. et al. |
| 2009/0124878 A1 | 5/2009 | Goode, Jr. et al. |
| 2009/0143661 A1* | 6/2009 | Taub et al. .................. 600/365 |
| 2009/0156924 A1 | 6/2009 | Shariati et al. |
| 2009/0177143 A1 | 7/2009 | Markle et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |

(56) References Cited

U.S. PATENT DOCUMENTS

| | | |
|---|---|---|
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2009/0287074 A1 | 11/2009 | Shults et al. |
| 2009/0299151 A1* | 12/2009 | Taub ............... A61B 5/14532 600/300 |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0045465 A1 | 2/2010 | Brauker et al. |
| 2010/0081908 A1 | 4/2010 | Dobbles et al. |
| 2010/0161269 A1 | 6/2010 | Kamath et al. |
| 2010/0240978 A1* | 9/2010 | LaBastide ............ A63F 13/005 600/365 |
| 2012/0035448 A1* | 2/2012 | Taub et al. ................ 600/365 |

FOREIGN PATENT DOCUMENTS

| | | |
|---|---|---|
| EP | 0 320 109 | 6/1989 |
| EP | 0 353 328 | 2/1990 |
| EP | 0 390 390 | 10/1990 |
| EP | 0 563 795 | 10/1993 |
| EP | 0 817 809 | 1/1998 |
| EP | 0 838 230 | 4/1998 |
| EP | 0 880 936 | 12/1998 |
| EP | 0 885 932 | 12/1998 |
| EP | 1 077 634 | 2/2001 |
| EP | 1 078 258 | 2/2001 |
| FR | 2656423 | 6/1991 |
| FR | 2760962 | 9/1998 |
| GB | 1 442 303 | 7/1976 |
| GB | 2149918 | 6/1985 |
| WO | WO 89/02720 | 4/1989 |
| WO | WO 90/00738 | 1/1990 |
| WO | WO 90/10861 | 9/1990 |
| WO | WO 92/13271 | 8/1992 |
| WO | WO 93/14693 | 8/1993 |
| WO | WO 94/22367 | 10/1994 |
| WO | WO 96/14026 | 5/1996 |
| WO | WO 96/25089 | 8/1996 |
| WO | WO 96/30431 | 10/1996 |
| WO | WO 97/01986 | 1/1997 |
| WO | WO 97/28737 | 8/1997 |
| WO | WO 98/24358 | 6/1998 |
| WO | WO 99/56613 | 4/1999 |
| WO | WO 99/48419 | 9/1999 |
| WO | WO 99/58051 | 11/1999 |
| WO | WO 99/58973 | 11/1999 |
| WO | WO 00/12720 | 3/2000 |
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 00/074753 | 12/2000 |
| WO | WO 00/78210 | 12/2000 |
| WO | WO 01/20019 | 3/2001 |
| WO | WO 01/20334 | 3/2001 |
| WO | WO 01/34243 | 5/2001 |
| WO | WO 01/52727 | 7/2001 |
| WO | WO 01/58348 | 8/2001 |
| WO | WO 01/68901 | 9/2001 |
| WO | WO 01/69222 | 9/2001 |
| WO | WO 01/88524 | 11/2001 |
| WO | WO 01/88534 | 11/2001 |
| WO | WO 02/24065 | 3/2002 |
| WO | WO 02/082989 | 10/2002 |
| WO | WO 02/100266 | 12/2002 |
| WO | WO 2005/011489 | 2/2005 |
| WO | WO 2005/012873 | 2/2005 |
| WO | WO 2005/057168 | 6/2005 |
| WO | WO 2005/057175 | 6/2005 |
| WO | WO 2005/026689 | 10/2005 |
| WO | WO 2006/105146 | 10/2006 |
| WO | WO 2008/076868 | 6/2008 |

OTHER PUBLICATIONS

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Anal. Chem. 64(18):2160-2163.

Abel et al. 1984. Experience with an implantable glucose sensor as a prerequisite of an artificial beta cell, Biomed. Biochim. Acta 43(5):577-584.

Abel et al. 2002. Biosensors for in vivo glucose measurement: can we cross the experimental stage. Biosens Bioelectron 17:1059-1070.

Adilman, Glenn, Videogames: Knowing the Score, Creative Computing, V9, p. 224(5), Dec. 1983, Dialog: File 148, Acc# 01891055.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers.com Nov. 7, 2006 http://www. Answers.com/topic/xenogenic.

Armour et al. Dec. 1990. Application of Chronic Intravascular Blood Glucose Sensor in Dogs. Diabetes 39:1519-1526.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosens Bioelectron 12:669-680.

Aussedat et al. 1997. A user-friendly method for calibrating a subcutaneous glucose sensor-based hypoglycaemic alarm. Biosensors & Bioelectronics 12(11):1061-1071.

Bailey et al. 2007. Reduction in hemoglobin A1c with real-time continuous glucose monitoring: results from a 12-week observational study. Diabetes Technology & Therapeutics 9(3):203-210.

Baker et al. 1993. Dynamic concentration challenges for biosensor characterization. Biosensors & Bioelectronics 8:433-441.

Baker et al. 1996. Dynamic delay and maximal dynamic error in continuous biosensors. Anal Chem 68(8):1292-1297.

Bani Amer, M. M. 2002. An accurate amperometric glucose sensor based glucometer with eliminated cross-sensitivity. J Med Eng Technol 26(5):208-213.

Bard et al. 1980. Electrochemical Methods. John Wiley & Sons, pp. 173-175.

Beach et al. 1999. Subminiature implantable potentiostat and modified commercial telemetry device for remote glucose monitoring. IEEE Transactions on Instrumentation and Measurement 48(6):1239-1245.

Bellucci et al. Jan. 1986. Electrochemical behaviour of graphite-epoxy composite materials (GECM) in aqueous salt solutions, Journal of Applied Electrochemistry, 16(1):15-22.

(56) References Cited

OTHER PUBLICATIONS

Bessman et al., Progress toward a glucose sensor for the artificial pancreas, Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diab. Thechnol. & Therapeut., 10:178-187.

Bindra et al. 1989. Pulsed amperometric detection of glucose in biological fluids at a surface-modified gold electrode. Anal Chem 61:2566-2570.

Bindra et al. 1991. Design and In Vitro Studies of a Needle-Type Glucose Senso for Subcutaneous Monitoring. Anal. Chem 63:1692-96.

Bisenberger et al. 1995. A triple-step potential waveform at enzyme multisensors with thick-film gold electrodes for detection of glucose and sucrose. Sensors and Actuators, B 28:181-189.

Bland et al. 1986. Statistical methods for assessing agreement between two methods of clinical measurement. Lancet 1:307-310.

Bland et al. 1990. A note on the use of the intraclass correlation coefficient in the evaluation of agreement between two methods of measurement. Comput. Biol. Med. 20(5):337-340.

Bobbioni-Harsch et al. 1993. Lifespan of subcutaneous glucose sensors and their performances during dynamic glycaemia changes in rats, J. Biomed. Eng. 15:457-463.

Bode et al. 1999. Continuous glucose monitoring used to adjust diabetes therapy improves glycosylated hemoglobin: A pilot study. Diabetes Research and Clinical Practice 46:183-190.

Bode et al. 2000. Using the continuous glucose monitoring system to improve the management of type 1 diabetes. Diabetes Technology & Therapeutics, 2(Suppl 1):S43-48.

Bode, B. W. 2000. Clinical utility of the continuous glucose monitoring system. Diabetes Technol Ther, 2(Suppl 1):S35-41.

Boedeker Plastics, Inc. 2009. Polyethylene Specifications Data Sheet, http://www.boedeker.com/polye_p.htm [Aug. 19, 2009 3:36:33 PM].

Boland et al. 2001. Limitations of conventional methods of self-monitoring of blood glucose. Diabetes Care 24(11):1858-1862.

Bolinder et al. 1992. Microdialysis measurement of the absolute glucose concentration in subcutaneous adipose tissue allowing glucose monitoring in diabetic patients. Diabetologia 35:1177-1180.

Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.

Bott, A. W. 1997. A Comparison of Cyclic Voltammetry and Cyclic Staircase Voltammetry Current Separations 16:1, 23-26.

Bott, A. 1998. Electrochemical methods for the determination of glucose. Current Separations 17(1):25-31.

Bowman, L.; Meindl, J. D. 1986. The packaging of implantable integrated sensors. IEEE Trans Biomed Eng BME33(2):248-255.

Brauker et al. 1996. Local Inflammatory Response Around Diffusion Chambers Containing Xenografts Transplantation 61(12):1671-1677.

Braunwald, 2008. Biomarkers in heart failure. *N. Engl. J. Med.*, 358: 2148-2159.

Bremer et al. 1999. Is blood glucose predictable from previous values? A solicitation for data. Diabetes 48:445-451.

Bremer et al. 2001. Benchmark data from the literature for evaluation of new glucose sensing technologies. Diabetes Technology & Therapeutics 3(3):409-418.

Brooks et al. "Development of an on-line glucose sensor for fermentation monitoring," Biosensors, 3:45-56 (1987/88).

Bruckel et al. 1989. In vivo measurement of subcutaneous glucose concentrations with an enzymatic glucose sensor and a wick method. Klin Wochenschr 67:491-495.

Brunstein et al. 1989. Preparation and validation of implantable electrodes for the measurement of oxygen and glucose. Biomed Biochim. Acta 48(11/12):911-917.

Cai et al. 2004. A wireless, remote query glucose biosensor based on a pH-sensitive polymer. Anal Chem 76(4):4038-4043.

Cameron et al. 1997. Micromodular Implants to provide electrical stimulation of paralyzed muscles and limbs. IEEE Transactions on Biomedical Engineering 44(9):781-790.

Campanella et al. 1993. Biosensor for direct determination of glucose and lactate in undiluted biological fluids. Biosensors & Bioelectronics 8:307-314.

Candas et al (1994). "An adaptive plasma glucose controller basedon on a nonlinear insulin/glucose model." *IEEE Transactions on Biomedical Engineering*, 41(2): 116-124.

Cass et al. "Ferrocene-mediated enzyme electrodes for amperometric determination of glucose," Anal. Chem., 36:667-71 (1984).

Cassidy et al., Apr. 1993. Novel electrochemical device for the detection of cholesterol or glucose, Analyst, 118:415-418.

Chase et al. 2001. Continuous subcutaneous glucose monitoring in children with type 1 diabetes. Pediatrics 107:222-226.

Chen et al. 2002. Defining the period of recovery of the glucose concentration after its local perturbation by the implantation of a miniature sensor. Clin. Chem. Lab. Med. 40:786-789.

Chia et al. 2004. Glucose sensors: toward closed loop insulin delivery. Endocrinol Metab Clin North Am 33:175-95.

Choleau et al. 2002. Calibration of a subcutaneous amperometric glucose sensor implanted for 7 days in diabetic patients. Part 1. Effect of measurement uncertainties on the determination of sensor sensitivity and background current . Biosensors and Bioel.

Choleau et al. 2002. Calibration of a subcutaneous amperometric glucose sensor implanted for 7 days in diabetic patients. Part 2. Superiority of the one-point calibration method. Biosensors and Bioelectronics 17:647-654.

Ciba® Irgacure 2959 Photoinitiator Product Description, Ciba Specialty Chemicals Inc., Basel, Switzerland.

Claremont et al. 1986. Subcutaneous implantation of a ferrocene-mediated glucose sensor in pigs. Diabetologia 29:817-821.

Claremont et al. Jul. 1986. Potentially-implantable, ferrocene-mediated glucose sensor. J. Biomed. Eng. 8:272-274.

Clark et al. 1981. One-minute electrochemical enzymic assay for cholesterol in biological materials, Clin. Chem. 27(12):1978-1982.

Clark et al. 1987. Configurational cyclic voltammetry: increasing the specificity and reliablity of implanted electrodes, IEEE/Ninth Annual Conference of the Engineering in Medicine and Biology Society, pp. 0782-0783.

Clark et al. 1988. Long-term stability of electroenzymatic glucose sensors implanted in mice. Trans Am Soc Artif Intern Organs 34:259-265.

Clarke et al. Sep.-Oct. 1987. Evaluating Clinical Accuracy of Systems for Self-Monitoring of Blood Glucose. Diabetes Care 10(5):622-628.

CLSI. Performance metrics for continuous interstitial glucose monitoring; approved guideline, CLSI document POCT05-A. Wayne, PA: Clinical and Laboratory Standards Institute: 2008 28(33), 72 pp.

Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.

Cox et al. 1985. Accuracy of perceiving blood glucose in IDDM. Diabetes Care 8(6):529-536.

Csöregi et al. 1994. Amperometric microbiosensors for detection of hydrogen peroxide and glucose based on peroxidase-modified carbon fibers. Electroanalysis 6:925-933.

Csoregi et al., 1994. Design, characterization, and one-point in vivo calibration of a subcutaneously implanted glucose electrode. Anal Chem. 66(19):3131-3138.

Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 1.

Danielsson et al. 1988. Enzyme thermistors, Methods in Enzymology, 137:181-197.

(56) References Cited

OTHER PUBLICATIONS

Dassau et al., In silico evaluation platform for artifical pancreatic β-cell development—a dynamic simulator for closed loop control with hardware-in-the-loop, Diabetes Technology & Therapeutics, 11(3):1-8, 2009.
Davies, et al. 1992. Polymer membranes in clinical sensor applications. I. An overview of membrane function, Biomaterials, 13(14):971-978.
Davis et al. 1983. Bioelectrochemical fuel cell and sensor based on a quinoprotein, alcohol dehydrogenase. *Enzyme Microb. Technol.*, vol. 5, September, 383-388.
Deutsch et al., "Time series analysis and control of blood glucose levels in diabetic patients". Computer Methods and Programs in Biomedicine 41 (1994) 167-182.
Diabetes Educational Video Game Recognized by Software Publishers Association, Press Release, Novo Nordisk, Mar. 14, 1994.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8: 121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanal. Chem. 373:758-761.
Fabietti et al. 2007. Clinical validation of a new control-oriented model of insulin and glucose dynamcs in subjects with type 1 diabetes, Diabetes Technology & Therapeutics, 9(4):327-338.
Fahy et al., An analysis: hyperglycemic intensive care patients need continuous glocuse monitoring—easier said than done, Journal of Diabetese Science and Technology, 2(2):201-204, Mar. 2008.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Fischer et al. 1995. Hypoglycaemia-warning by means of subcutaneous electrochemical glucose sensors: an animal study, Horm. Metab. Rese. 27:53.
Freedman et al. 1991. Statistics, Second Edition, W.W. Norton & Company, p. 74.
Freiberger, Paul, Video Game Takes on Diabetes Superhero 'Captain Novolin' Offers Treatment Tips, San Francisco Examiner, Jun. 26, 1992, Fourth Edition, Business Sec. B1.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.

Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.
Ganesh et al., Evaluation of the VIA® blood chemistry monitor for glucose in healthy and diabetic volunteers, Journal of Diabetese Science and Technology, 2(2):182-193, Mar. 2008.
Garg et al. 1999. Correlation of fingerstick blood glucose measurements with GlucoWatch biographer glucose results in young subjects with type 1 diabetes. Diabetes Care 22(10):1708-1714.
Garg et al. 2004. Improved Glucose Excursions Using an Implantable Real-Time continuous Glucose Sensor in Adults with Type I Diabetes. Diabetes Care 27:734-738.
Gerritsen et al. 1999. Performance of subcutaneously implanted glucose sensors for continuous monitoring. The Netherlands Journal of Medicine 54:167-179.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004, Feasibility of continuous long-term glucose monitoring from a subcutaneous glucose sensor in humans. Diabetes Technol Ther 6:378-386.
Godsland et al. 2001. Maximizing the Success Rate of Minimal Model Insulin Sensitivity Measurement in Humans: The Importance of Basal Glucose Levels. The Biochemical Society and the Medical Research Society, 1-9.
Gouda et al., Jul. 4, 2003. Thermal inactiviation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C.*
Heise et al. 2003. Hypoglycemia warning signal and glucose sensors: Requirements and concepts. Diabetes Technology & Therapeutics 5:563-571.
Heller, "Electrical wiring of redox enzymes," *Acc. Chem. Res.*, 23:128-134 (1990).
Heller, A. 1992. Electrical Connection of Enzyme Redox Centers to Electrodes. J. Phys. Chem. 96:3579-3587.

(56) References Cited

OTHER PUBLICATIONS

Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hicks, 1985. In Situ Monitoring, Clinical Chemistry, 31(12):1931-1935.
Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Anal Chem 75:3308-3315.
http://www.merriam-webster.com/dictionary, *definition for "aberrant,"* Aug. 19, 2008, p. 1.
Hu, et al. 1993. A needle-type enzyme-based lactate sensor for in vivo monitoring, Analytica Chimica Acta, 281:503-511.
Huang et al. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.
Hunter et al. 2000. Minimally Invasive Glucose Sensor and Insulin Delivery System. MIT Home Automation and Healthcare Consortium. Progress Report No. 25.
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.
Jablecki et al. 2000. Simulations of the frequency response of implantable glucose sensors. Analytical Chemistry 72:1853-1859.
Jaremko et al. 1998. Advances toward the implantable artificial pancreas for treatment of diabetes. Diabetes Care 21(3):444-450.
Jensen et al. 1997. Fast wave forms for pulsed electrochemical detection of glucose by incorporation of reductive desorption of oxidation products. Analytical Chemistry 69(9):1776-1781.
Jeong et al. 2003. In vivo calibration of the subcutaneous amperometric glucose sensors using a non-enzyme electrode. Biosensors and Bioelectronics 19:313-319.
Jeutter, D. C. 1982. A transcutaneous implanted battery recharging and biotelemeter power switching system. IEEE Trans Biomed Eng 29:314-321.
Jeutter et al. 1993. Design of a radio-linked implantable cochlear prosthesis using surface acoustic wave devices. IEEE Transactions on ultrasonics, ferroelectrics and frequency control 40(5):469-477.
Johnson (1991). "Reproducible electrodeposition of biomolecules for the fabrication of miniature electroenzymatic biosensors," *Sensors and Actuators B*, 5:85-89.
Johnson et al. 1992. In vivo evaluation of an electroenzymatic glucose sensor implanted in subcutaneous tissue. Biosensors & Bioelectronics, 7:709-714.
Joung et al. 1998. An energy transmission system for an artificial heart using leakage inductance compensation of transcutaneous transformer. IEEE Transactions on Power Electronics 13(6):1013-1022.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kamath et al. Calibration of a continuous glucose monitor: effect of glucose rate of change, Eighth Annual Diabetes Technology Meeting, Nov. 13-15, 2008, p. A88.
Kang et al. 2003. In vitro and short-term in vivo characteristics of a Kel-F thin film modified glucose sensor. Anal Sci 19:1481-1486.
Kaufman. 2000. Role of the continuous glucose monitoring system in pediatric patients. Diabetes Technology & Therapeutics 2(1):S-49-S-52.
Kaufman et al. 2001. A pilot study of the continuous glucose monitoring system. Diabetes Care 24(12):2030-2034.
Kawagoe et al. 1991. Enzyme-modified organic conducting salt microelectrode, Anal. Chem. 63:2961-2965.
Keedy et al. 1991. Determination of urate in undiluted whole blood by enzyme electrode. *Biosensors & Bioelectronics*, 6: 491-499.
Kerner et al. 1988. A potentially implantable enzyme electrode for amperometric measurement of glucose, Horm Metab Res Suppl. 20:8-13.
Kerner et al. 1993. "The function of a hydrogen peroxide-detecting electroenzymatic glucose electrode is markedly impaired in human sub-cutaneous tissue and plasma," Biosensors & Bioelectronics, 8:473-482.
Kerner, W. 2001. Implantable glucose sensors: Present status and future developments. Exp. Clin. Endocrinol. Diabetes 109(Suppl 2):S341-346.
Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.
Ko, Wen H. 1985. Implantable Sensors for Closed-Loop Prosthetic Systems, Futura Pub. Co., Inc., Mt. Kisco, NY, Chapter 15:197-210.
Kondo et al. 1982. A miniature glucose sensor, implantable in the blood stream. Diabetes Care. 5(3):218-221.
Koschinsky et al. 1988. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activitiy, swelling, and permeability studies, Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.
Kraver et al. 2001. A mixed-signal sensor interface microinstrument. Sensors and Actuators A 91:266-277.
Krouwer, J. S. 2002. Setting performance goals and evaluating total analytical error for diagnostic assays. Clinical Chemistry 48(6):919-927.
Kruger et al. 2000. Psychological motivation and patient education: A role for continuous glucose monitoring. Diabetes Technology & Therapeutics, 2(Suppl 1):S93-97.
Kulys et al., 1994. Carbon-paste biosensors array for long-term glucose measurement, Biosensors& Beioelectronics, 9:491-500.
Kunjan et al., Automated blood sampling and glocuse sensing in critical care settings, Journal of Diabetes Science and Technology 2(3):194-200, Mar. 2008.
Kurnik et al. 1999. Application of the mixtures of experts algorithm for signal processing in a noninvasive glucose monitoring system. Sensors and Actuators B, 60:19-26.
Kurtz et al. 2005. Recommendations for blood pressure measurement in humans and experimental animals, Part 2: Blood pressure measurement in experimental animals, a statement for professionals from the subcommittee of professional and public education of.
LaCourse et al. 1993. Optimization of waveforms for pulsed amperometric detection of carbohydrates based on pulsed voltammetry. Analytical Chemistry 65:50-52.
Ladd et al., Structure Determination by X-ray Crystallography, 3rd ed. Plenum, 1996, Ch. 1, pp. xxi-xxiv and 1-58.
Lehmann et al. May 1994. Retrospective valication of a physiological model of glucose-iunsulin interaaction in tyhpe 1 diabetes mellitus, Med. Eng. Phys. 16:193-202.

(56) References Cited

OTHER PUBLICATIONS

Lerner et al. 1984. An implantable electrochemical glucose sensor. Ann. N. Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Lohn et al., A knowledge-based system for real-time validation of calibrations and measurements, Chemometrics and Intelligent Laboratory Systems, 1999 46, 57-66.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. *Diabetes Technology & Therapeutics*, 10(4): 257-265.

Lynch et al. 2001. Estimation-based model predictive control of blood glucose in type I diabetics: A simulation study. Proceedings of the IEEE 27th Annual Northeast Bioengineering Conference, pp. 79-80.

Lynn, P. A. 1971. Recursive digital filters for biological signals. Med. & Biol. Engng. 9:37-43.

Maidan et al. 1992. Elimination of Electrooxidizable Interferent-Produced Currents in Amperometric Biosensors, Analytical Chemistry, 64:2889-2896.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Mancy et al. 1962. A galvanic cell oxygen analyzer. Journal of Electroanalytical Chemistry 4:65-92.

Maran et al. 2002. Continuous subcutaneous glucose monitoring in diabetic patients: A multicenter analysis. Diabetes Care 25(2):347-352.

Mar., W. F. 2002. Dealing with the delay. Diabetes Technol Ther 4(1):49-50.

Marena et al. 1993. The artifical endocrine pancreas in clinical practice and research. Panminerva Medica 35(2):67-74.

Martin, R. F. 2000. General Deming regression for estimating systematic bias and its confidence interval in method-comparison studies. *Clinical Chemistry*, 46(1):100-104.

Mascini et al. 1989. Glucose electrochemical probe with extended linearity for whole blood. *J Pharm Biomed Anal* 7(12): 1507-1512.

Mastrototaro et al. 1991 "An electroenzymatic glucose sensor fabricated on a flexible substrate," Sensors and Actuators B, 5:139-44.

Mastrototaro, J. J. 2000. The MiniMed continuous glucose monitoring system. Diabetes Technol Ther 2(Suppl 1):S13-8.

Mastrototaro et al. 2003. Reproducibility of the continuous glucose monitoring system matches previous reports and the intended use of the product. Diabetes Care 26:256; author reply p. 257.

Matsuki. 1994. Energy transfer system utilizing amorphous wires for implantable medical devices. IEEE Transactions on Magnetics 31(2):1276-1282.

Matsumoto et al. 1998. A micro-planar amperometeric glucose sensor unsusceptible to interference species. Sensors and Actuators B 49:68-72.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

Mazzola et al., Video Diabetes: A Teaching Tool for Children with Insulin-Dependent Diabetes, Proceedings—7th Annual Symposium on Computer Applications in Medical Care; Washington, D.C.; Dialog:, (Oct. 1983), File 8, Acc# 01624462.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

McKean, et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Merriam-Webster Online Dictionary. Definition of "acceleration". http://www.merriam-webster.com/dictionary/Acceleration Jan. 11, 2010.

Merriam-Webster Online Dictionary. Definition of "system". http://www.merriam-webster.com/dictionary/System Jan. 11, 2010.

Merriam-Webster Online Dictionary. The term "nominal." http://www.m-w.com/dictionary/nominal.

Metzger et al. Jul. 2002. Reproducibility of glucose measurements using the glucose sensor. Diabetes Care 25(6):1185-1191.

Meyerhoff et al. 1992. On line continuous monitoring of subcutaneous tissue glucose in men by combining portable glucosensor with microdialysis. Diabetologia 35:1087-1092.

Miller et al. 1993. Development of an autotuned transcutaneous energy transfer system ASAIO Journal 39:M706-M710.

Moatti-Sirat et al. 1992. Evaluating in vitro and in vivo the interference of ascorbate and acetaminophen on glucose detection by a needle-type glucose sensor, Biosensors & Bioelectronics 7:345-352.

Moatti-Sirat et al. 1992. Towards continuous glucose monitoring: in vivo evaluation of a miniaturized glucose sensor implanted for several days in rat subcutaneous tissue. Diabetologia 35:224-230.

Moatti-Sirat et al., Reduction of acetaminophen interference in glucose sensors by a composite Nafion membrane: demonstration in rats and man, Diabetologia 37(6):610-616, Jun. 1994.

Monsod et al. 2002. Do sensor glucose levels accurately predict plasma glucose concentrations during hypoglycemia and hyperinsulinemia? Diabetes Care 25(5):889-893.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme termistor and its use for the assay of metobolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Moussy et al. 1994. A miniaturized Nafion-based glucose sensor: In vitro and in vivo evaluation in dogs. Int. J. Artif. Organs 17(2):88-94.

Murphy, et al. 1992. Polymer membranes in clinical sensor applications. II. The design and fabrication of permselective hydrogels for electrochemical devices, Biomaterials, 13(14):979-990.

Muslu. 1991. Trickling filter performance. Apllied Biochemistry and Biotechnology 37:211-224.

Nafion® 117 Solution Product Description, Product No. 70160, Sigma-Aldrich Corp., St. Louis, MO.

Neuburger et al. 1987. Pulsed amperometric detection of carbohydrates at gold electrodes with a two-step potential waveform. Anal. Chem. 59:150-154.

Nintendo Healthcare, Wired, Dec. 1993.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

(56) References Cited

OTHER PUBLICATIONS

Ohara et al. 1994. "Wired" enzyme electrodes for amperometric determination of glucose or lactate in the presence of interfering substances. Anal Chem 66:2451-2457.
Okuda et al. 1971. Mutarotase effect on micro determinations of D-glucose and its anomers with β-D-glucose oxidase. Anal Biochem 43:312-315.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Panteleon et al. 2003. The role of the independent variable to glucose sensor calibration. Diabetes Technology & Therapeutics 5(3):401-410.
Parker et al. 1999. A model-based algorithm for blood glucose control in type I diabetic patients. IEEE Trans. Biomed. Eng. 46(2):148-157.
Patel et al. 2003. Amperometric glucose sensors based on ferrocene containing polymeric electron transfer systems-a preliminary report. Biosens Bioelectron 18:1073-6.
Peacock et al. 2008. Cardiac troponin and outcome in acute heart failure. N. Engl. J. Med., 358: 2117-2126.
Pfeiffer, E.F. 1990. The glucose sensor: the missing link in diabetes therapy, Horm Metab Res Suppl. 24:154-164.
Pfeiffer et al. 1992. On line continuous monitoring of subcutaneous tissue glucose is feasible by combining portable glucosensor with microdialysis. Horm. Metab. Res. 25:121-124.
Philips. 1995. A high capacity transcutaneous energy transmission system. ASAIO Journal 41:M259-M262.
Pichert et al. 2000. Issues for the coming age of continuous glucose monitoring Diabetes Educ 26(6):969-980.
Pickup et al. "Implantable glucose sensors: choosing the appropriate sensing strategy," Biosensors, 3:335-346 (1987/88).
Pickup et al. "In vivo molecular sensing in diabetes mellitus: an implantable glucose sensor with direct electron transfer," Diabetologia, 32:213-217 (1989).
Pickup et al. 1989. Potentially-implantable, amperometric glucose sensors with mediated electron transfer: improving the operating stability. Biosensors 4:109-119.
Pickup et al. 1993. Responses and Calibration of Amperometric Glucose Sensors Implanted in the Subcutaneous Tissue of Man. ACTA Diabetol, pp. 143-148.
Pickup et al. 1993. Developing glucose sensors for in vivo use. Elsevier Science Publishers Ltd (UK), TIBTECH vol. 11: 285-291.
Pinner et al., Cross-linking of cellulose acetate by ionizing radiation, Nature, vol. 184, 1303-1304, Oct. 24, 1959.
Pishko et al. 1991. "Amperometric glucose microelectrodes prepared through immobilization of glucose oxidase in redox hydrogels," Anal. Chem., 63:2268-72.
Pitzer et al. 2001. Detection of hypoglycemia with the GlucoWatch biographer. Diabetes Care 24(5):881-885.
Poirier et al. 1998. Clinical and statistical evaluation of self-monitoring blood glucose meters. Diabetes Care 21(11):1919-1924.
Poitout et al. 1991. In Vitro and In Vivo Evaluation in Dogs of a Miniaturized Glucose Sensor, ASAIO Transactions, 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Raya Systems Pioneers Healthy Video Games, PlayRight, Nov. 1993 (pp. 14-15).
Reach et al. 1986. A Method for Evaluating in vivo the Functional Characteristics of Glucose Sensors. Biosensors 2:211-220.
Reach et al. 1992. Can continuous glucose monitoring be used for the treatment of diabetes? Analytical Chemistry 64(5):381-386.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. "Automated feedback control of subcutaneous glucose concentration in diabetic dogs," Diabetologia, 32:573-76 (1989).
Rebrin et al. 1992. Subcutaenous glucose monitoring by means of electrochemical sensors: fiction or reality? J. Biomed. Eng. 14:33-40.
Rebrin et al. 1999. Subcutaneous glucose predicts plasma glucose independent of insulin: Implications for continuous monitoring. Am. J. Physiol. 277:E561-71.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assitance improves glycemic control and glucose stability in pump-treated patients. Diab. Thechnol. & Therapeut., 10:194-199.
Rinken et al. 1998. Calibration of glucose biosensors by using pre-steady state kinetic data. Biosensors & Bioelectronics, 13:801-807.
Rivers et al., Central venous oxygen saturation monitoring in the critically ill patient, Current Opinion in Critical Care, 7:204-211, 2001.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sakakida et al. 1993. Ferrocene-Mediated Needle Type Glucose Sensor Covered with Newly Designed Biocompatible Membran, Sensors and Actuators B 13-14:319-322.
Salardi et al. 2002. The glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.
Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1992. Calibration of a wearable glucose sensor. The International Journal of Artificial Organs 15(1):55-61.
Schmidt et al. 1993. Glucose concentration in subcutaneous extracellular space. Diabetes Care 16(5):695-700.
Schmidtke et al. 1998. Accuracy of the one-point in vivo calibration of "wired" glucose oxidase electrodes implanted in jugular veins of rats in periods of rapid rise and decline of the glucose concentration. Anal Chem 70:2149-2155.

(56) References Cited

OTHER PUBLICATIONS

Schmidtke et al., Measurement and modeling of the transient difference between blood and subcutaneous glucose concentrations in the rat after injection of insulin. *Proc Natl Acad Sci U S A* 1998, 95, 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Service et al. 1970. Mean amplitude of glycemic excursions, a measure of diabetic instability. Diabetes, 19: 644-655.
Service et al. 1987. Measurements of glucose control. Diabetes Care, 10: 225-237.
Service, R. F. 2002. Can sensors make a home in the body? Science 297:962-3.
Sharkawy et al. 1996. Engineering the tissue which encapsulates subcutaneous implants. I. Diffusion properties, J Biomed Mater Res, 37:401-412.
Shaw et al. "In vitro testing of a simply constructed, highly stable glucose sensor suitable for implantation in diabetic patients," Biosensors & Bioelectronics, 6:401-406 (1991).
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors 197-210.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al. 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Skyler, J. S. 2000. The economic burden of diabetes and the benefits of improved glycemic control: The potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.
Smith et al. 1998. An externally powered, multichannel, implantable stimulator-telemeter for control of paralyzed muscle. IEEE Transactions on Biomedical Engineering 45(4):463-475.
Sokol et al. 1980, Immobilized-enzyme rate-determination method for glucose analysis, Clin. Chem. 26(1):89-92.
Sokolov et al. 1995. Metrological opportunities of the dynamic mode of operating an enzyme amperometric biosensor. Med. Eng. Phys. 17(6):471-476.
Sparacino et al., 2008. Continuous glucose monitoring time series and hypo/hyperglycemia prevention: requirements, methods, open problems, Current Diabetes Reviews, 4:181-192.
Sproule et al. 2002. Fuzzy pharmacology: Theory and applications. Trends in Pharmacological Sciences, 23(9):412-417.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sternberg et al. 1988. Study and Development of Multilayer Needle-type Enzyme-based Glucose Microsensors. Biosensors 4:27-40.

Sternberg et al. 1996. Does fall in tissue glucose precede fall in blood glucose? Diabetologia 39:609-612.
Street et al. 1988. A note on computing robust regression estimates via iteratively reweighted least squares. The American Statistician 42(2):152-154.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tamura, T. et al. 2000. Preliminary study of continuous glucose monitoring with a microdialysis technique and a null method—a numerical analysis. Frontiers Med. Biol. Engng. 10(2):147-156.
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome et al. 1995.—Abstract—Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Thome-Duret et al. 1996. Use of a subcutaneous glucose sensor to detect decreases in glucose concentration prior to observation in blood, Anal. Chem. 68:3822-3826.
Thomé-Duret et al. 1998. Continuous glucose monitoring in the free-moving rat. Metabolism, 47:799-803.
Thompson et al., In Vivo Probes: Problems and Perspectives, Department of Chemistry, University of Toronto, Canada, pp. 255-261, 1986.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: A frequent, automatic and noninvasive glucose monitor. Ann. Med. 32:632-641.
Tilbury et al. 2000. Receiver operating characteristic analysis for intelligent medical systems—A new approach for finding confidence intervals. IEEE Transactions on Biomedical Engineering 47(7):952-963.
Torjman et al., Glucose monitoring in acute care: technologies on the horizon, Journal of Deabetes Science and Technology, 2(2):178-181, Mar. 2008.
Trajanoski et al. 1998. Neural predictive controller for insulin delivery using the subcutaneous route. IEEE Transactions on Biomedical Engineering 45(9):1122-1134.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.
Turner and Pickup, "Diabetes mellitus: biosensors for research and management," *Biosensors*, 1:85-115 (1985).
Unger et al. 2004. Glucose control in the hospitalized patient. Emerg Med 36(9):12-18.
Updike et al. 1967. The enzyme electrode. Nature, 214:986-988.
Updike et al. 1979. Continuous glucose monitor based on an immobilized enzyme electrode detector. J Lab Clin Med, 93(4):518-527.
Updike et al. 1982. Implanting the glucose enzyme electrode: Problems, progress, and alternative solutions. Diabetes Care, 5(3):207-212.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.

(56) References Cited

OTHER PUBLICATIONS

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Valdes et al. 2000. In vitro and in vivo degradation of glucose oxidase enzyme used for an implantable glucose biosensor. Diabetes Technol. Ther. 2:367-376.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Wagner et al. 1998. Continuous amperometric monitoring of glucose in a brittle diabetic chimpanzee with a miniature subcutaneous electrode. Proc. Natl. Acad. Sci. A, 95:6379-6382.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 1999. Assessment of chronically implanted subcutaneous glucose sensors in dogs: The effect of surrounding fluid masses. ASAIO Journal, 45:555-561.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2000. Rise in background current over time in a subcutaneous glucose sensor in the rabbit: Relevance to calibration and accuracy. Biosensors & Bioelectronics, 15:53-61.
Ward et al. 2002. A new amperometric glucose microsensor: In vitro and short-term in vivo evaluation. Biosensors & Bioelectronics, 17:181-189.
Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Integrated implantable device for long-term glucose monitoring. Biosens. Bioelectron 10:485-494.
Wilkins et al. 1996. Glucose monitoring: state of the art and future possibilities. Med Eng Phys 18:273-288.
Wilson et al. 1992. Progress toward the development of an implantable sensor for glucose. Clin. Chem. 38(9):1613-1617.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Wu et al. 1999. In situ electrochemical oxygen generation with an immunoisolation device. Annals New York Academy of Sciences, pp. 105-125.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.
Yang et al (1996). "A glucose biosensor based on an oxygen electrode: In-vitro performances in a model buffer solution and in blood plasma," Biomedical Instrumentation & Technology, 30:55-61.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal of Membrane Science 237:145-161.
Ye et al. 1993. High Current Density 'Wired' Quinoprotein Glucose Dehydrogenase Electrode. Anal. Chem. 65:238-241.
Zamzow et al. 1990. Development and evaluation of a wearable blood glucose monitor, ASAIO Transactions; 36(3): pp. M588-M591.
Zavalkoff et al. 2002. Evaluation of conventional blood glucose monitoring as an indicator of integrated glucose values using a continuous subcutaneous sensor. Diabetes Care 25(9):1603-1606.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2O_2$ on Pt and Pt+Ir electrodes in physiological buffer and its applicability to $H_2O_2$-based biosensors. J. Electroanal. Chem., 345:253-271.
Zhang et al. 1993. In vitro and in vivo evaluation of oxygen effects on a glucose oxidase based implantable glucose sensor. Analytica Chimica Acta, 281:513-520.
Zhang et al. 1994. Elimination of the acetaminophen interference in an implantable glucose sensor. Analytical Chemistry 66(7):1183-1188.
Zhu et al. (1994). "Fabrication and characterization of glucose sensors based on a microarray $H_2O_2$ electrode." *Biosensors & Bioelectronics*, 9: 295-300.
Zhu et al. 2002. Planar amperometric glucose sensor based on glucose oxidase immobilized by chitosan film on prussian blue layer. Sensors, 2:127-136.
Ziaie et al. 1997. A single-channel implantable microstimulator for functional neuromuscular stimulation. IEEE Transactions on Biomedical Engineering 44(10):909-920.
Office Action dated Sep. 30, 2002 in U.S. Appl. No. 09/636,369.
Office Action dated Jul. 15, 2008 in U.S. Appl. No. 10/633,367.
Office Action dated Jun. 11, 2009 in U.S. Appl. No. 10/633,367.
Office Action dated Jul. 30, 2009 in U.S. Appl. No. 12/102,654.
Office Action dated Mar. 10, 2010 in U.S. Appl. No. 12/102,654.
Office Action dated Dec. 23, 2008 in U.S. Appl. No. 12/102,745.
Office Action dated Oct. 20, 2004 in U.S. Appl. No. 10/632,537.
Office Action dated Dec. 21, 2004 in U.S. Appl. No. 10/632,537.
Office Action dated May 29, 2008 in U.S. Reexam. No. 95/001,039.
Office Action dated Jun. 17, 2008 in U.S. Appl. No. 11/038,340.
Office Action dated Jan. 5, 2009 in U.S. Appl. No. 11/038,340.
Office Action dated May 19, 2009 in U.S. Appl. No. 11/038,340.
Office Action dated Nov. 9, 2009 in U.S. Appl. No. 11/038,340.
Office Action dated Feb. 2, 2010 in U.S. Appl. No. 11/038,340.
Office Action dated Jun. 7, 2010 in U.S. Appl. No. 11/038,340.
Office Action dated Feb. 12, 2007 in U.S. Appl. No. 10/633,404.
Office Action dated Jun. 17, 2008 in U.S. Reexam. No. 95/001,038.
Office Action dated May 28, 2010 in U.S. Reexam. No. 95/001,038.
Office Action dated Oct. 5, 2006 in U.S. Appl. No. 10/633,329.
Office Action dated Mar. 26, 2007 in U.S. Appl. No. 10/633,329.
Office Action dated Jul. 30, 2007 in U.S. Appl. No. 10/633,329.

(56) References Cited

OTHER PUBLICATIONS

Office Action dated Feb. 4, 2008 in U.S. Appl. No. 10/633,329.
Office Action dated Jun. 12, 2008 in U.S. Appl. No. 10/633,329.
Office Action dated Dec. 18, 2008 in U.S. Appl. No. 10/633,329.
Office Action dated Jun. 11, 2009 in U.S. Appl. No. 10/633,329.
Office Action dated Apr. 27, 2010 in U.S. Appl. No. 10/633,329.
Office Action dated Jun. 23, 2009 in U.S. Appl. No. 10/648,849.
Office Action dated Jun. 24, 2008 n U.S. Appl. No. 11/007,920.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Oct. 3, 2008 in U.S. Appl. No. 10/789,359.
Office Action mailed Jun. 5, 2008 in U.S. Appl. No. 10/838,909.
Office Action mailed Mar. 16, 2009 in U.S. Appl. No. 10/838,909.
Office Action dated Mar. 31, 2008 in U.S. Appl. No. 11/077,759.
Office Action dated Jul. 10, 2008 in U.S. Appl. No. 11/077,759.
Office Action dated May 26, 2009 in U.S. Appl. No. 11/077,759.
Office Action dated Jul. 21, 2009 in U.S. Appl. No. 11/077,739.
Office Action dated Dec. 29, 2009 in U.S. Appl. No. 11/077,739.
Office Action dated Mar. 1, 2010 in U.S. Appl. No. 11/077,739.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Jul. 25, 2008 in U.S. Appl. No. 11/077,740.
Office Action dated Apr. 28, 2009 in U.S. Appl. No. 11/077,740.
Office Action dated Dec. 31, 2007 in U.S. Appl. No. 11/077,765.
Office Action dated May 16, 2008 in U.S. Appl. No. 11/077,765.
Office Action dated Sep. 19, 2008 in U.S. Appl. No. 11/077,765.
Office Action dated Jan. 23, 2009 in U.S. Appl. No. 11/077,765.
Office Action dated Feb. 3, 2010 in U.S. Appl. No. 11/077,765.
Office Action dated Jun. 26, 2008 in U.S. Appl. No. 11/157,365.
Office Action dated Jan. 7, 2009 in U.S. Appl. No. 11/157,365.
Office Action dated Jul. 21, 2009 in U.S. Appl. No. 11/157,365.
Office Action dated Jan. 21, 2010 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated May 2, 2008 in U.S. Appl. No. 11/334,876.
Office Action dated Aug. 26, 2008 in U.S. Appl. No. 11/334,876.
Office Action dated Aug. 25, 2009 in U.S. Appl. No. 11/334,876.
Office Action dated Jun. 30, 2008 in U.S. Appl. No. 11/360,252.
Office Action dated Jan. 29, 2009, in U.S. Appl. No. 11/360,252.
Office Action dated Jul. 23, 2009, in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.
Office Action dated Oct. 29, 2009 in U.S. Appl. No. 11/360,819.
Office Action dated Apr. 7, 2010 in U.S. Appl. No. 11/360,819.
ISR and WO dated May 26, 2010 for PCT/US2010/028927, filed Mar. 26, 2010.
IPRP dated Sep. 27, 2011 for PCT/US2010/028927, filed Mar. 26, 2010.
Direct 30/30® Blood Glucose Sensor, (Markwell Medical) Catalog, © 1990, ELCO Diagnostics Company.
Huang et al., "A 0.5mW Passive Telemetry IC for Biomedical Applications," Proceedings of the 23rd European Solid-State Circuits Conference (ESSCIRC '97), pp. 172-175, Sep. 1997, Southampton, UK.
Merriam-Webster Online Dictionary. Definition of "nominal." http://www.m-w.com/dictionary/nominal Apr. 23, 2007.
Nafion® 117 Solution Product Description, Product No. 70160, Sigma-Aldrich Corp., St. Louis, MO. Apr. 7, 2005.
Official Communication in European App. No. 06748336.2, dated Jun. 16, 2010.
Office Action dated Jul. 7, 2010 in U.S. Appl. No. 12/098,359.
Office Action dated Jun. 28, 2010 in U.S. Appl. No. 12/182,073.
Office Action dated Jun. 24, 2010 in U.S. Appl. No. 12/182,083.
Office Action dated Jun. 25, 2010 in U.S. Appl. No. 12/536,852.

\* cited by examiner

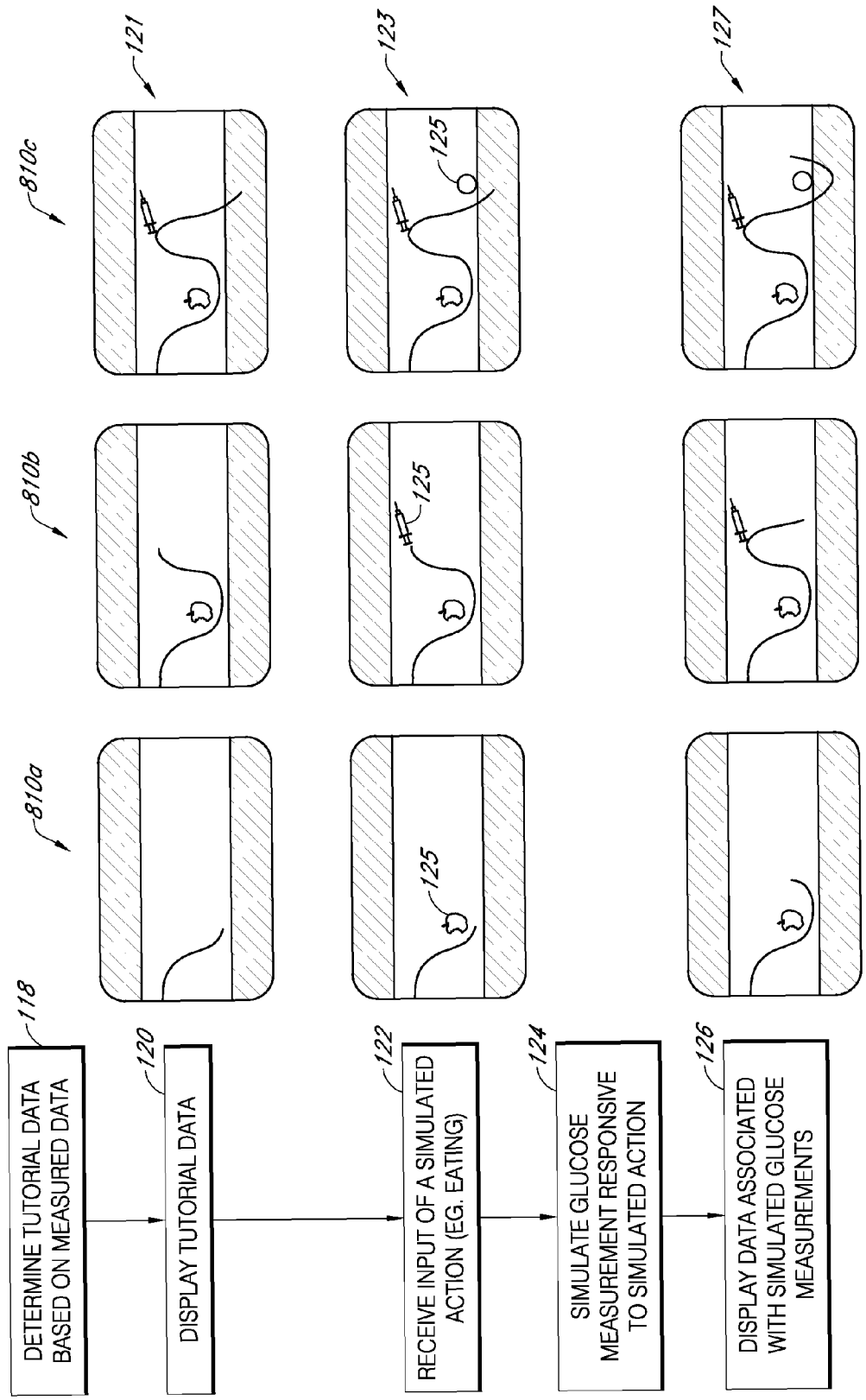

METHODS AND SYSTEMS FOR PROMOTING GLUCOSE MANAGEMENT

CROSS REFERENCE TO RELATED APPLICATIONS

This application claims priority to Provisional Application 61/164,326, filed on Mar. 27, 2009. The disclosure of this application is hereby incorporated by reference in its entirety.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes will normally only measure his or her glucose levels two to four times per day. Unfortunately, these time intervals are so far apart that the person with diabetes will likely find out too late about hyper- or hypo-glycemic conditions. In fact, it is not only unlikely that a person with diabetes will take a timely SMBG value, it is likely that the person with diabetes will not know if their blood glucose value is going up (higher) or down (lower) based on conventional methods. Thus, their ability to make educated insulin therapy decisions is inhibited.

Some attempts have been made to continuously measure the glucose concentration in a person with diabetes. More frequent measurements can allow the person with diabetes to know of essentially current blood sugar conditions and to make appropriate decisions in response to the current conditions. However, these continuous glucose sensors typically use methods of displaying measurement data which is uninteresting to the person with diabetes. This is especially the case when the person with diabetes is young. Pediatric persons with diabetes often do not understand, forget about, or intentionally ignore the data displayed from their continuously measured glucose monitor. Accordingly, people with diabetes experience blood sugar excursions which may have been avoided had they been more diligently interacting with their sensor system.

Accordingly, there exists a need for improvements in displaying data from continuous glucose sensors in order to better entice the person with diabetes, such as pediatric patients, to use and interact with their monitor system.

SUMMARY

In one embodiment, the invention comprises a method of encouraging interactions with a receiver configured to receive sensor data from a glucose sensor. The method comprises sensing an interaction from a user with a receiver, wherein the receiver is configured to receive sensor data from the glucose sensor and to selectively display information associated with the sensor data and/or the sensor data in response to interactions from the user. In response to a plurality of different sensed interactions, a reward counter is incremented, and in response to determining that the reward counter has reached a predetermined reward threshold, a reward indication on the receiver is displayed, and/or a reward indication is transmitted.

In another embodiment, a method of encouraging interactions with a continuous glucose monitoring system comprises sensing a user interaction with a portion of the continuous glucose monitoring system and incrementing a reward counter in response to the sensed interaction independent of the creation or value of any sensor data.

In another embodiment, a portable sensor system is provided. The sensor system comprises a glucose sensor configured to provide real-time continuous glucose sensor data, a device comprising a user interface configured to receive user input and display the real time glucose sensor data responsive to user-interaction with the portable device, and a processor module configured to tabulate a score based at least in part on user interactions with the user interface.

BRIEF DESCRIPTION OF THE DRAWINGS

FIG. 8A is a flowchart that illustrates a process of displaying tutorial data for a user.

FIG. 8B illustrates exemplary frames of a tutorial.

DETAILED DESCRIPTION OF CERTAIN EMBODIMENTS

Figure 1:
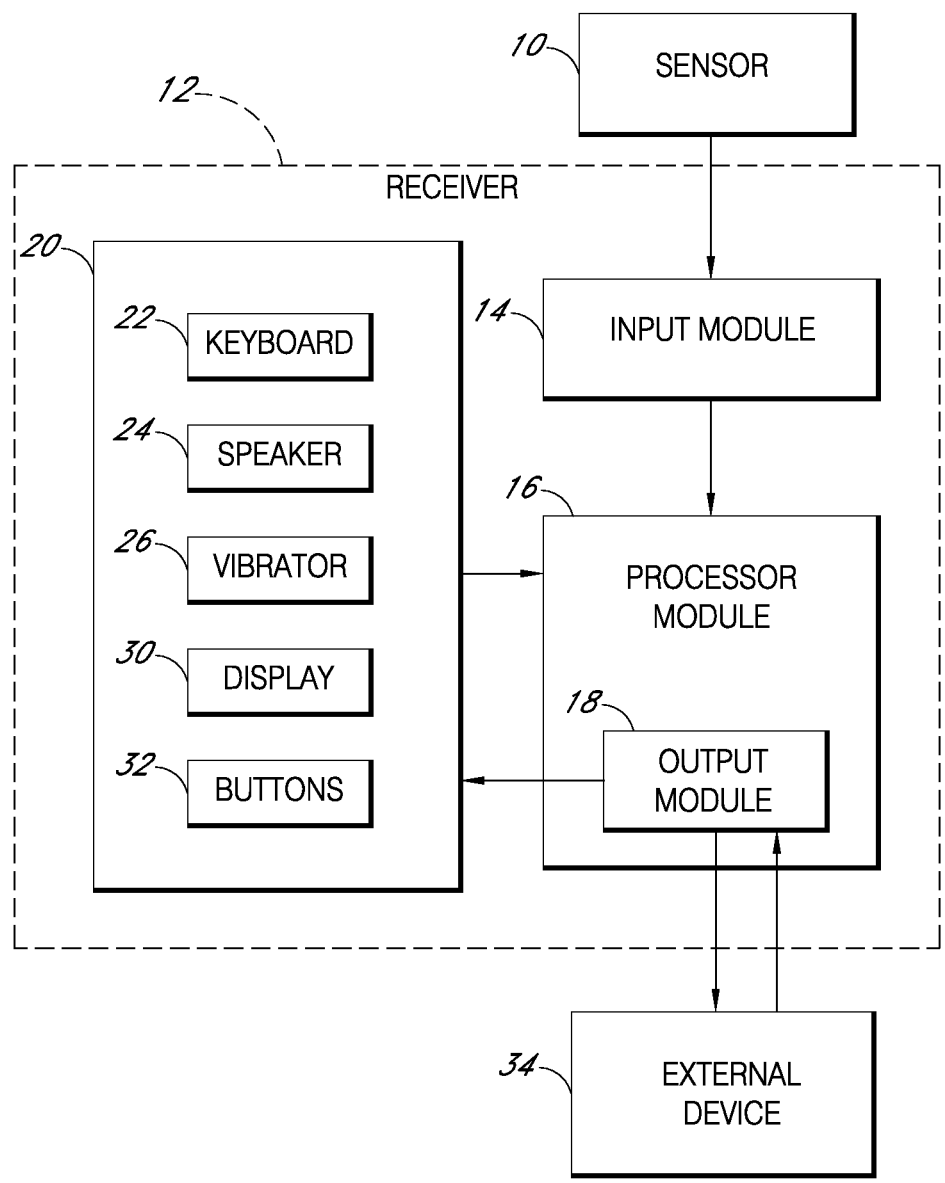
FIG. 1 is a block diagram that illustrates a configuration of a medical device in one embodiment, including a continuous analyte sensor, a receiver, and an external device.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "analyte," as used herein, is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "continuous analyte sensor," as used herein, is a broad term and is used in its ordinary sense, including, but not limited to, a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte sensing," as used herein, is a broad term and is used in its ordinary sense, including, but not limited to, monitoring of an analyte continuously, for example, at time intervals ranging from fractions of a second up to, for example, 1, 2, or 5 minutes, or longer.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "calibration" as used herein is a broad term and is to be given its ordinary and customary meaning to a person of ordinary skill in the art (and is not to be limited to a special or customized meaning), and furthermore refers without limitation to a process of determining a relationship between sensor data and corresponding reference data, which can be used to convert sensor data into calibrated data (defined below). In some embodiments, such as continuous analyte sensors, for example, calibration can be updated or recalibrated over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "time period," as used herein, is a broad term and is used in its ordinary sense, including, but not limited to, an amount of time including a single point in time and a path (for example, range of time) that extends from a first point in time to a second point in time.

The term "measured analyte values," as used herein, is a broad term and is used in its ordinary sense, including, but not limited to, an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The term "estimated analyte values," as used herein, is a broad term and is used in its ordinary sense, including, but not limited to, an analyte value or set of analyte values, which have been algorithmically extrapolated from measured analyte values. Typically, estimated analyte values are estimated for a time period during which no data exists. However, estimated analyte values can also be estimated during a time period for which measured data exists, but is to be replaced by algorithmically extrapolated data due to a time lag in the measured data, for example.

The term "alarm," as used herein, is a broad term and is used in its ordinary sense, including, but not limited to, audible, visual, or tactile signals that are triggered in response to detection of clinical risk to a patient. In one embodiment, hyperglycemic and hypoglycemic alarms are triggered when present or future clinical danger is assessed based on continuous analyte data.

The terms "target analyte values" and "analyte value goal," as used herein, are broad terms and are used in their ordinary sense, including, but not limited to, an analyte value or set of analyte values that are clinically acceptable. In one example, a target analyte value is visually or audibly presented to a patient in order to aid in guiding the patient in understanding how they should avoid a clinically risky analyte concentration.

The terms "therapy" and "therapy recommendations," as used herein, are broad terms and are used in their ordinary sense, including, but not limited to, the treatment of disease or disorder by any method. In one exemplary embodiment, a patient is prompted with therapy recommendations such as "inject insulin" or "consume carbohydrates" in order to avoid a clinically risky glucose concentration.

The term "computer," as used herein, is broad term and is used in its ordinary sense, including, but not limited to, machine that can be programmed to manipulate data.

The term "modem," as used herein, is a broad term and is used in its ordinary sense, including, but not limited to, an electronic device for converting between serial data from a computer and an audio signal suitable for transmission over a telecommunications connection to another modem.

The term "insulin pen," as used herein, is a broad term and is used in its ordinary sense, including, but not limited to, an insulin injection device generally the size of a pen that includes a needle and holds a vial of insulin. It can be used instead of syringes for giving insulin injections.

The term "insulin pump," as used herein, is a broad term and is used in its ordinary sense, including, but not limited to, a device that delivers a continuous supply of insulin into the body. The insulin flows from the pump through a plastic tube (called a catheter) that is connected to a needle inserted into the skin and taped in place, for example.

Overview

Certain embodiments provide a continuous analyte sensor that measures a concentration of analyte within a host and provides a data stream representative of the concentration of the analyte in the host, and a receiver that processes the data stream received from the analyte sensor for output as part of a user interface that is displayed on a display of the receiver, for example. In some embodiments, the analyte sensor is integral with the receiver, while in other embodiments, the analyte sensor is operatively linked to the receiver, for example, via a wired link or a wireless link.

Sensor data associated with a host may be displayed in a variety of manners that are interesting to the user, and are configured to motivate the user to interact with the receiver, for example, pediatric users. For example, the data may be depicted with graphical indicia so as to form a scene unrelated to glucose measurement. In some embodiments, the scene may form a real-life picture or an animation of an event. In some embodiments, the data may be depicted with an interactive animation, video game or cartoon. For example, the data may be depicted as a series of frames associated with a game or a cartoon that changes in accordance with changes in sensor data. The graphics displayed on the frames may include rewards based on actions taken by the user or based on sensor data. The data displayed may be used as a tutorial for educational interaction between the sensor system and the host. In some embodiments, data may be displayed with an avatar, an icon, or other character that is recognizable to the host. In some embodiments, therapy recommendations can be provided that are useful in guiding the host away from clinical risk. Interesting and/or intuitive display methods can help users to be more involved and aware of their glucose levels. This increased awareness provides the user with better recognition of current glucose trends and therefore better ability to react to and to control glucose excursions.

In some embodiments, the receiver casts diabetes management as a game in which users can earn and lose points according to their glycemic control over a length of time. The game may be played with instructions, such as "avoid glucose excursions outside target range for high score." Points may be earned for each sensor data point indicating a glucose level that falls within the target range. In some embodiments, points may be lost for each sensor data point indicating a glucose level above or below the target range. Scores may be tallied for a fixed period of time, such as 24 hours, 1 week, 1 month, 3 months or more, and compared from period to period. In some embodiments, the number of excursions that occur after a game begins may limit the duration of the game. For example, the user may be allowed 3 excursions before the game is over, at which time the final score is tallied. With improved scores, the target ranges may be tightened to encouraged further improvement. In some embodiments, game scores may be related to clinical measures of glycemic control, such as HbA1c, and provide users and their caregivers continuous assessment of their diabetes management.

In some embodiments, a receiver generates user interfaces that are based on and/or include real-time sensor data, such as measured analyte values, transformed sensor data, estimated analyte values, possible variations of estimated analyte values, targets or goals for analyte values, single-point values and/or the like. Additionally or alternatively, user interfaces and/or data that is useable to generate user interfaces, can be sent to a device external from the receiver, for example, a mobile computing device of a caretaker of the host, a computer, an electronic medical records system, a modem, or medical device. In some embodiments, input from the user or from another device, such as insulin injections (time and amount), meal times, exercise, personalized therapy recommendations, or the like, can be input into the receiver and processed to provide more customized data analysis and/or data output.

Accordingly, the systems and methods described herein display sensor data in such a way as to entice interaction between the user and the sensor system. This may increase the likelihood that the host will recognize that they are in a state, e.g., hypoglycemia or hyperglycemia, for which some action should be taken for their benefit.

Continuous Sensor

In some embodiments, a glucose sensor comprises an analyte sensor that measures a concentration of analyte of interest or a substance indicative of the concentration or presence of the analyte. A glucose sensor may use any known method, including invasive, minimally invasive, and non-invasive sensing techniques, to provide an output signal indicative of the concentration of the analyte of interest. In some embodiments, a glucose sensor comprises a continuous analyte sensor, for example a subcutaneous, transdermal, or intravascular device. In some embodiments, a glucose sensor can take a plurality of intermittent measurements. An analyte sensor can use any method of analyte-measurement, including enzymatic, chemical, physical, electrochemical, spectrophotometric, polarimetric, calorimetric, radiometric, or the like. Generally, an analyte sensor can be any sensor capable of determining the level of any analyte in the body, for example glucose, oxygen, lactase, hormones, cholesterol, medicaments, viruses, or the like. It should be understood that the devices and methods described herein can be applied to any device capable of continually or continuously detecting a concentration of analyte and providing an output signal that represents the concentration of that analyte.

In one embodiment, an analyte sensor is an implantable glucose sensor, such as described with reference to U.S. Pat. No. 6,001,067 and co-pending U.S. Patent Publication 2005/0027463 which are incorporated herein by reference in their entirety. In another embodiment, an analyte sensor is a transcutaneous glucose sensor, such as described with reference to U.S. Provisional Patent Application 60/587,787 and 60/614,683. In one alternative embodiment, the continuous glucose sensor comprises a transcutaneous sensor such as described in U.S. Pat. No. 6,565,509 to Say et al., for example. In another alternative embodiment, a continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, a continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al. All of the above patents are incorporated by reference herein in their entirety. Other signal processing techniques and glucose monitoring system embodiments suitable for use with the inventions described herein are also described in U.S. Patent Publications 2005/0203360 and 2009/0192745, both of which are incorporated herein by reference in their entireties.

FIG. 1 is a block diagram that illustrates a receiver 12 in communication with a sensor 10 and an external device 34. In general, the continuous analyte sensor 10 is any sensor configuration that provides an output signal indicative of a concentration of an analyte. The output signal (e.g., sensor data, such as a raw data stream, filtered data, smoothed data, and/or otherwise transformed sensor data) is sent to the receiver 12 and received by an input module 14, which is described in more detail below. The output signal may include a raw data stream that is used to provide a useful value of the measured analyte concentration to a patient or doctor, for example. In some embodiments, the sensor data from the sensor 10 can be continuously or periodically algorithmically smoothed, calibrated, or otherwise modified to diminish outlying points that do not accurately represent the analyte concentration, for example due to signal noise or other signal artifacts, such as described in co-pending U.S. Pat. No. 6,931,327, which is incorporated herein by reference in its entirety.

Receiver

Referring again to FIG. 1, the receiver 12, which is operatively linked to the sensor 10, receives a data stream from the sensor 10 via the input module 14. In one embodiment, the input module 14 includes a quartz crystal operably connected to an RF transceiver (not shown) that together function to receive and synchronize data streams from the sensor 10. However, the input module 14 can be configured in any manner that is capable of receiving data from the sensor. Once received, the input module 14 sends the data stream to a processor 16 that processes the data stream, such as described in more detail below.

The processor 16 is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, or the like. The processor includes hardware that performs the processing described herein, for example read-only memory (ROM) provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing.

An output module 18, which may be integral with and/or operatively connected with the processor 16, includes programming for generating output based on the sensor data received from the sensor 10 and its processing incurred in the processor 16. In some embodiments, output is generated via one or more input/output devices 20.

The input/output devices 20 of this embodiment comprise a keyboard 22, speaker 24, vibrator 26, backlight 28, display device 30, and one or more buttons 32. The components that comprise the input/output devices 20 include controls to allow interaction of the user with the receiver. The keyboard 22 can allow, for example, input of user information about himself/herself, such as mealtime, insulin and carbohydrate ratios, exercise, insulin administration, customized therapy recommendations, and reference analyte values. The speaker 24 can produce, for example, audible signals or alerts for conditions such as present and/or estimated hyper- and hypoglycemic conditions in a person with diabetes. The vibrator 26 can provide, for example, tactile signals or alerts for reasons such as described with reference to the speaker, above. In some embodiments, the display device 30 is a touch-sensitive screen. The buttons 32 can provide for toggle, menu selection, option selection, mode selection, and reset, for example. In some alternative embodiments, a microphone can be provided to allow for voice-activated control.

In some embodiments, analyte values are displayed on the display device 30. In some embodiments, prompts or messages can be displayed on the display device 30 to convey information to the user, such as reference outlier values, requests for reference analyte values, therapy recommendations, deviation of the measured analyte values from the estimated analyte values, or the like. Additionally, prompts can be displayed to guide the user through calibration or trouble-shooting of the calibration.

Additionally, data output from the output module 18 can provide wired or wireless, one- or two-way communication between the receiver 12 and an external device 34. The external device 34 can be any device that interfaces or communicates with the receiver 12. In some embodiments, the external device 34 is a computer, and the receiver 12 is able to download historical data for retrospective analysis by the physician, for example. In some embodiments, the external device 34 is a modem, and the receiver 12 is able to send alerts, warnings, emergency messages, or the like, via telecommunication lines to another party, such as a doctor or family member. In some embodiments, the external device 34 is an insulin pen, and the receiver 12 is able to communicate therapy recommendations, such as insulin amount and time to the insulin pen. In some embodiments, the external device 34 is an insulin pump, and the receiver 12 is able to communicate therapy recommendations, such as insulin amount and time to the insulin pump. The external device 34 can include other technology or medical devices, for example pacemakers, implanted analyte sensor patches, other infusion devices, telemetry devices, or the like. The receiver 12 may communicate with the external device 34, and/or any number of additional external devices, via any suitable communication protocol, including radio frequency, Bluetooth, universal serial bus, any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, and/or a proprietary communication protocol.

The input/output devices 20 including keyboard 22, buttons 32, a microphone (not shown), as well as the external device 34, can be configured to allow input of data. Data input can be helpful in obtaining information about the patient (for example, meal time, exercise, or the like), receiving instructions from a physician (for example, customized therapy recommendations, targets, or the like), and downloading software updates, for example. Keyboard, buttons, touch-screen, and microphone are all examples of mechanisms by which a user can input data directly into the receiver. A server, personal computer, personal digital assistant, insulin pump, and insulin pen are examples of external devices that can provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual.

In a further embodiment, input/output devices can be used to generate data for tracking physical exercise performed by the host. In this regard, a global positioning device (GPS) and/or accelerometer can be incorporated internally with or communicatively coupled externally to receiving unit 12 to provide positional and/or movement data of a host. Other sensors, such as a heart monitor, can also be used either alone or in combination with the GPS and accelerometer, to provide exercise-related data for tracking exercise performed by the host. In doing so, types of rewards and reward values can be tracked and awarded based partly or wholly on exercise performed by the host, as discussed in more detail later in this disclosure.

While a few examples of data input have been provided here, a variety of information can be input, which can be helpful in data processing as will be understood by one skilled in the art.

Customized User Interfaces Depicting Sensor Data

A data stream received from a continuous analyte sensor can provide an analyte value and/or other sensor data, and display the same to the host, which can be used to warn the host (or other interested party, such as a caretaker of the host or doctor) of existing clinical risk. A data stream received from an analyte sensor can provide historical trend analyte values, which can be used to educate a patient, caretaker, and/or doctor of individual historical trends of the patient's analyte concentration.

Sensor data may be displayed in such a way as to be more interesting to the user than a line graph, for example. In one embodiment, for example, sensor data may be depicted as a series of frames of a game, an animation, or a cartoon. The display may include rewards based on actions taken by the user or based on measurement data. The data displayed may be used as a tutorial for educational interaction between the sensor system and the user. In some embodiments, data may be displayed and/or otherwise conveyed (e.g., spoken instruction may be emitted from the speaker 24 of the receiver 12) by an avatar, an icon or a character depicted on the display device 30.

In some embodiments, receivers, such as receiver 12 of FIG. 1 have multiple games which can be selected by the user. In some embodiments, the game is selected randomly or pseudorandomly. Each game may have graphics which are used by the receiver 12 to display the frames of the game, where each frame comprises a depiction of graphical and/or textual data on a display device. The graphics associated with each game may be game-specific or may be applied to multiple games. The graphics may be used to represent one or more aspects of sensor data received from a sensor, such as sensor 10 of FIG. 1, and to represent game context information for the sensor data.

Figure 2:
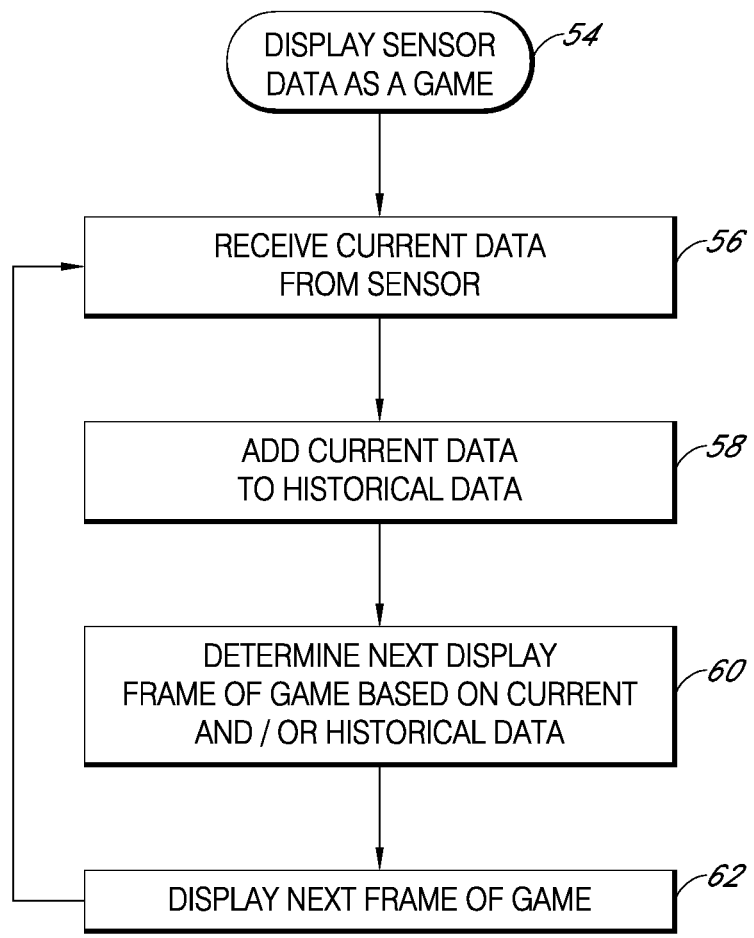
FIG. 2 is a flowchart that illustrates a process of displaying sensor data as a game.

FIG. 2 is a flowchart illustrating one embodiment of a method 54 of displaying sensor data as a game or a cartoon. The process is used by, for example, a receiver, such as receiver 12 of FIG. 1 to display a user interface that incorporates and/or is based on sensor data received. The process 54 includes receiving current sensor data from the sensor, which is the data point or data set most recently received, adding the received current sensor data to previously received data, determining a next frame to display based on the current sensor data and/or the previously received sensor data, and displaying the frame. In some embodiments, the receiver 12 generates graphical data indicative of a sequence of historical sensor data, as well as current sensor data, in a currently displayed frame. Depending on the embodiment, the method of FIG. 3 may include fewer or additional blocks and the blocks may be performed in a different order than is illustrated.

At block 56, current sensor data is received from the sensor 10. At block 58, the current sensor data is added to a memory containing sensor data received previously. The current sensor data and the previously received sensor data collectively form stored sensor data, which is used at block 60 to determine a next frame of the game. The sensor data may, for example, represent a glucose level, or a range of levels. In some embodiments, the sensor data is displayed with a resolution corresponding to the uncertainty of the measurement.

Each frame may be determined based on one or more selected sets of sensor data of the stored sensor data. The selection of a data set for determining a next frame may be based on a certain time frame. For example, the most recent sensor data may be selected. For example, the sensor data taken in the most recent 1 hour, 3 hours, 6 hours, day, week, month, or year may be selected. Sensor data in other most recent times may also be used. In some embodiments, sensor data received since a reference time may be selected. The reference time may include such times as when waking up, going to sleep, eating a meal, exercising, or taking insulin. Other reference times may be used. In some embodiments, sensor data received during specified time periods may be selected. For example, sensor data received between 1 pm and 5 pm on one or more days may be selected. Other time periods may be used.

In one embodiment, a host's glucose response associated with a consistent event, such as lunch, is analyzed such that a carbohydrate (referred to also as a "carb") estimate and insulin amount given, for example, are analyzed to determine a "typical" lunch size. For example, the insulin delivery information may be more accurate, with the time to action being the key variable such that reasonable estimates for that might estimate not only the typical, approximate meal size, but also the diversity of the meal (all carbs, high fat, etc.) based on the response, thereby allowing more customization for bolus calculation in the future based on "typical" meals. In one embodiment, hosts estimate a meal size (small, medium or large, for example) and/or meal makeup (high fat, high carb, low carb, balanced carb/fat/protein, etc.), and the sensor electronics may determine insulin delivery based on "learned" knowledge of the particular patients behavior and "typical" meal size and response.

In some embodiments, the selection of sensor data for a data set is based on the content of the sensor data, such as characteristics of transformed sensor data. For example, in some embodiments, sensor data taken over a specified time having glucose levels within a specified measurement range are selected and/or sensor data between upper and lower thresholds are selected. In some embodiments, sensor data greater than or less than a certain threshold are selected. The thresholds may, for example, correspond to blood glucose target range boundaries.

In some embodiments, the selected sensor data for a data set is selected based on processed data. For example, in some embodiments, raw sensor data is processed to determine rates of change in blood glucose levels for each time point for which sensor data is acquired, and data for the data set are selected for times when the rate of change in the sensor data meets certain criteria. For example, sensor data taken when the rate of change in the blood glucose levels is greater than a certain limit, less than a certain limit, or within a certain range may be selected. As another example, average glucose values for days of the past month during which the rate of change in data does not exceed a threshold may be selected for a data set. In some embodiments, the average values for days of the past month during which the rate of change in data does exceed a threshold may be also be selected as a second data set.

The selected one or more data sets are used in conjunction with graphics associated with the current game to determine the next frame of the game. For example, a selected data set may be represented with a series of frames, where each frame of the series depicts one or more data points, e.g. blood glucose levels, of the selected data set. In some embodiments, the most recent data point is represented with a first graphic and the historical data is represented as multiple second graphics. In addition, game context graphics may also be determined based on the current game and the previous frames of the game. In some embodiments, the game context graphics include graphics which represent target range boundaries. The range boundaries may be defined through an interface to a database storing the boundary data. The range boundaries may be defined by a caretaker of a child with diabetes via a computing device in communication with the child's receiver, for example. Thus, operation of the games may be customized according to the particular characteristics of the host.

In some embodiments, the game context graphics include graphics which represent a qualitative or quantitative assessment of performance. For example, a score can be shown, or an estimated HbA1c value. Other assessment graphics include a character having a smiling face or a frowning face, and/or a variation in a color of a graphic. In some embodiments, game context graphics include a target, which indicates a desired analyte level or analyte performance characteristic.

At block 62, graphics illustrative of at least portions of the selected one or more data sets are displayed in the next frame. In some embodiments, a sequence of frames is shown to generate an animation or a cartoon. For example, a series of frames, each depicting a subset of the selected data set may be shown sequentially, such that each successive frame shows more of the selected data. The series may be displayed in response to an input from the user.

Figure 3A:
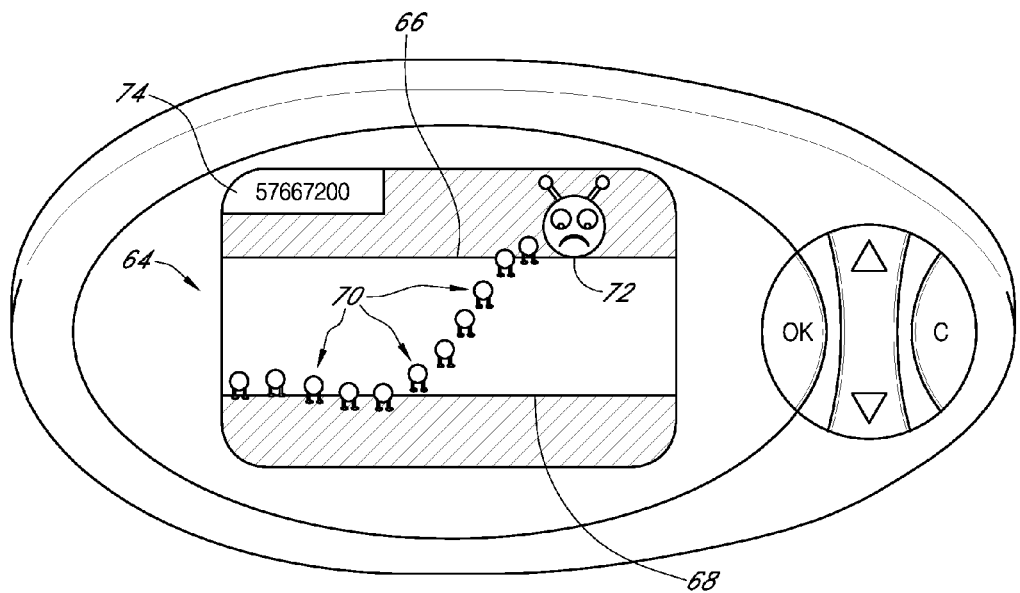
FIGS. 3A-3H are drawings illustrating various embodiments of displayed sensor data.

FIG. 3A is a drawing illustrating an embodiment of a frame 64 representing sensor data. The frame 64 includes a graphic 66 representing an upper limit of a target range for the host's glucose level, a graphic 68 representing a lower limit of the target range for the host's glucose level, a series 70 of graphics representing historical glucose level measurements, a graphic 72 representing the most recent measurement, and a graphic 74 representing an assessment of performance. In this embodiment, the graphics 70 and 72 cooperatively represent a centipede, where the centipede comprises body segment graphics 70 associated with historical sensor data, and a head graphic 72 associated with the latest sensor data. In this embodiment, the head graphic 72 has a face which is frowning because the latest glucose level is outside of a desired target range. In this embodiment, graphic 74 represents an assessment of performance as a numerical score.

Figure 3B:
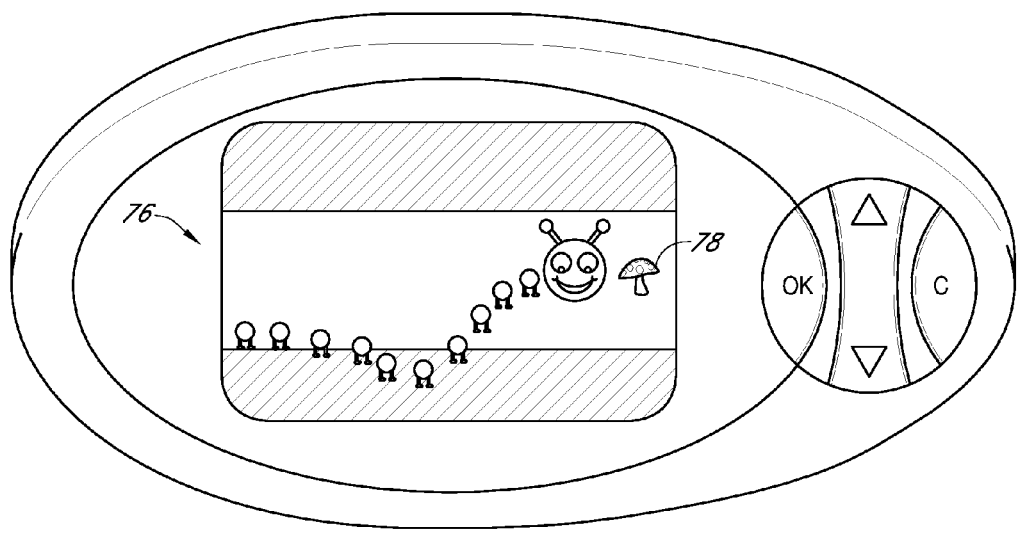

FIG. 3B is a drawing illustrating an embodiment of a frame 76 representing sensor data. Frame 76 includes a target graphic 78, which indicates a desired glucose level or range of glucose levels In some embodiments, the target graphic 78 can change positions from frame to frame in order to entice better analyte control from the user.

Figure 3C:
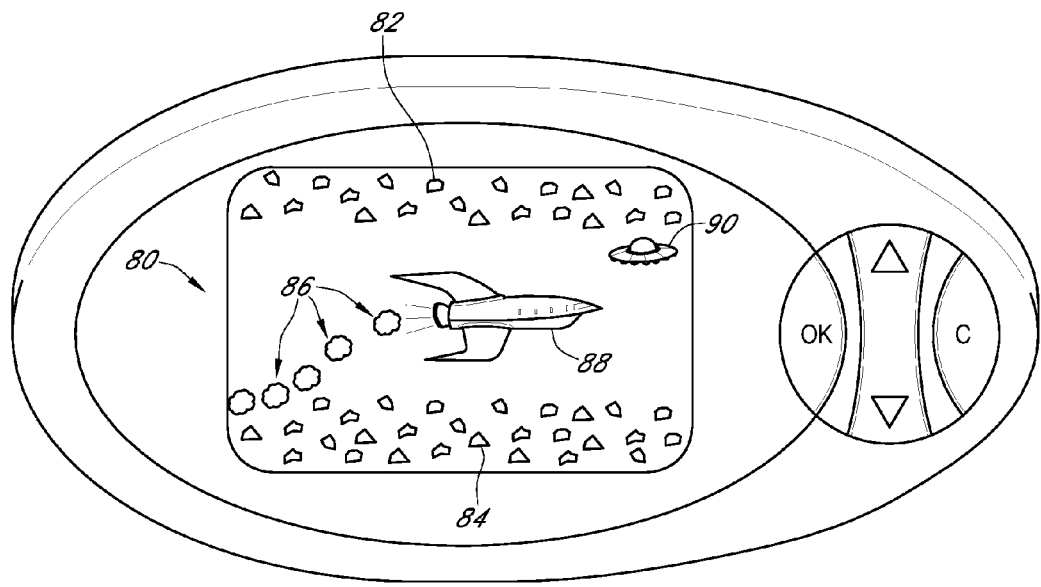

FIG. 3C is a drawing illustrating an embodiment of a frame 80 representing sensor data. The frame 80 includes a graphic 82 representing a higher than target range for the host's glucose level, a graphic 84 representing a lower than target range for the host's glucose level, a series 86 of graphics representing historical glucose levels, a graphic 88 representing the latest glucose level, and a graphic 90 representing a target glucose level. Depending on the embodiment, the frames of a game (e.g., FIGS. 2 and 3) may be updated in response to each newly received sensor data point or set, after a predetermined quantity of sensor data points or sets are received (e.g., a new frame is provided after five sensor data points or sets are received by the receiver), and/or in response to receiving sensor data matching a predefined criteria (e.g., a glucose level that is approaching a hypoglycemic level). In the embodiment of FIG. 3C, the graphic 90 is at the high end of the target range so as to entice the user to generate higher glucose levels.

Figure 3D:
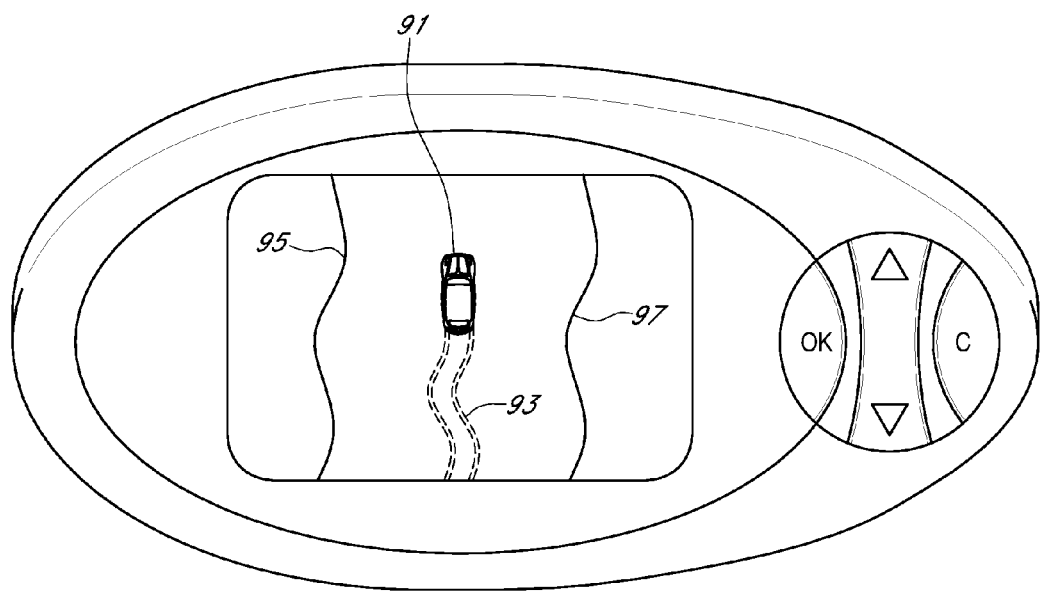
Figure 3E:
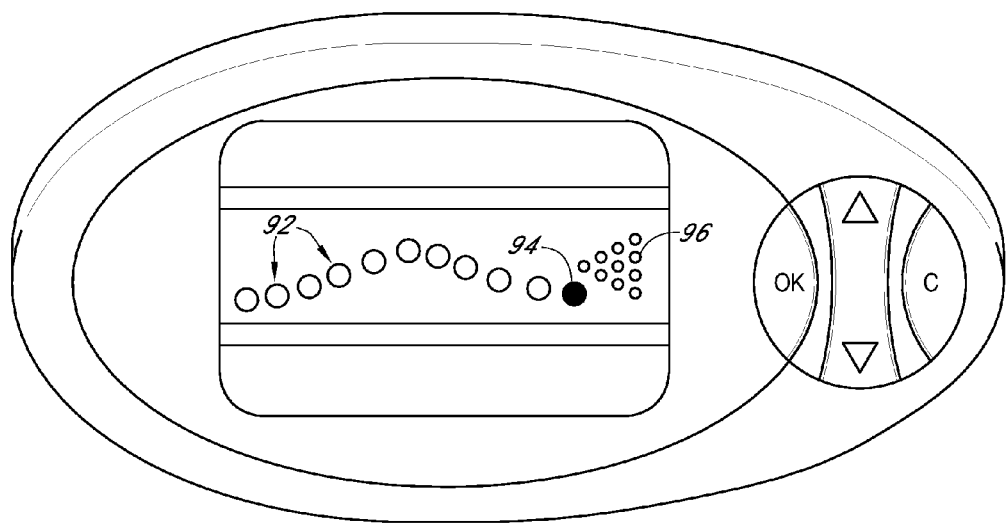

FIG. 3D is a drawing representing another exemplary frame illustrating graphics representative of historical and current sensor data. In this embodiment a vehicle graphic 91 represents the latest sensor data and a plurality of a track graphics 93 represent historical sensor data. The graphics 95 and 97 represent the boundaries of the desired target range, such as the sides of a road or racetrack, and may be generally vertical. In other embodiments, the boundaries, e.g., sides of the road, may be generally horizontal. In the illustrated embodiment, graphics 95 and 97 are non-linear. The non-linear boundaries can be used to further entice the user to achieve preferred glucose levels. In other embodiments, the boundaries (e.g., similar to graphics 95 and 97), which illustrates the sides of a road or racetrack, for example, may be non-linear, but parallel, or the boundaries may be linear. Depending of the embodiment, the boundaries may be user-settable and may be representative of a target glucose levels or ranges and/or may be representative of an alarm level (e.g. alert setting for hypo- or hyper-glycemia actual, predicted, or near).

Figure 3F:
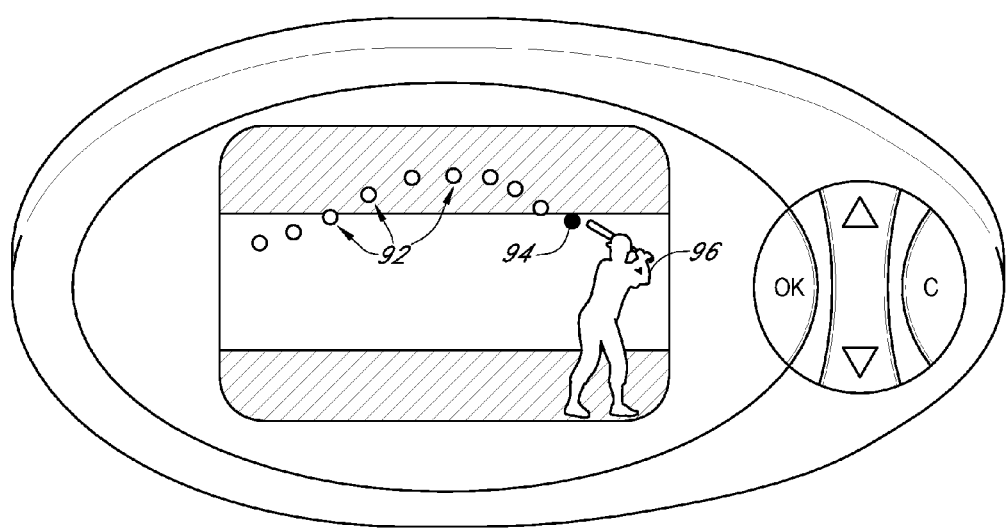
Figure 3G:
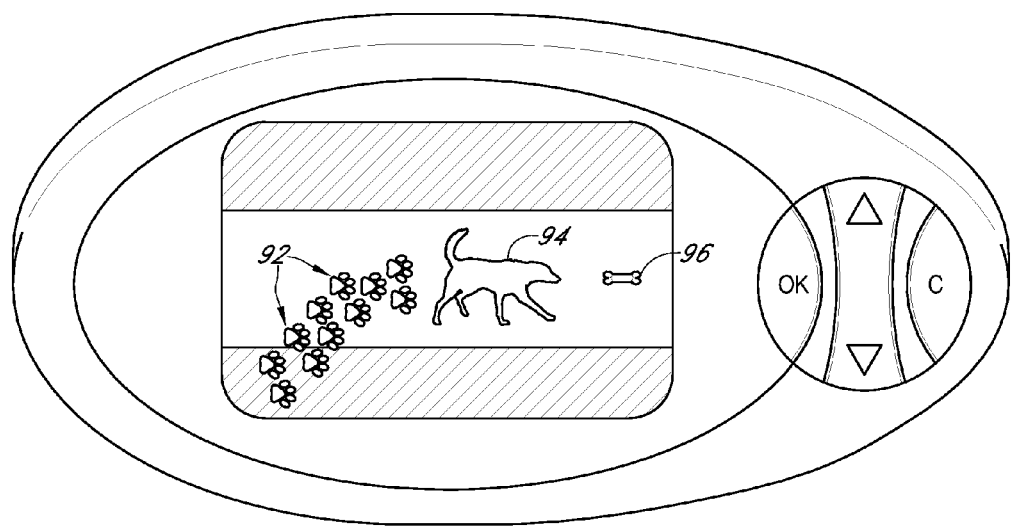
Figure 3H:
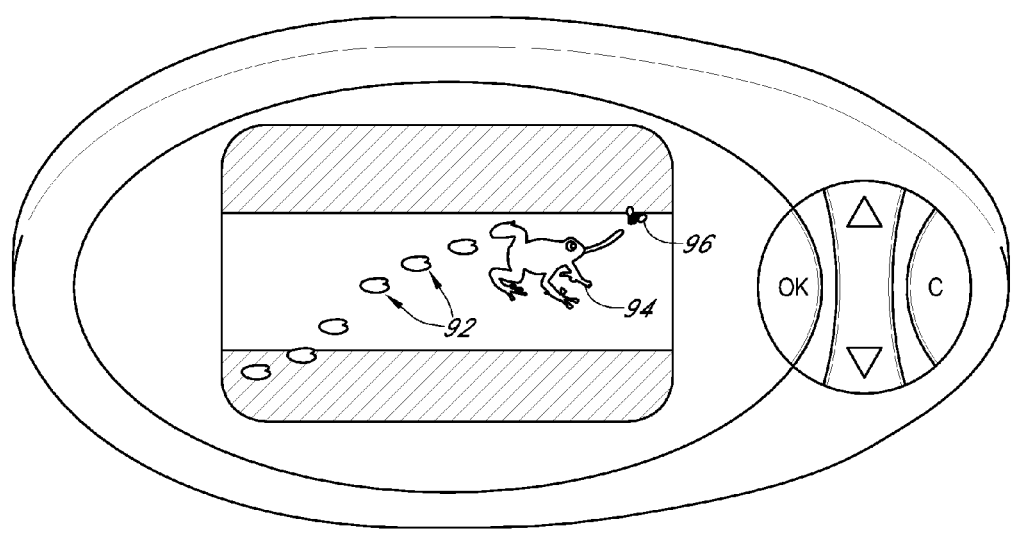
Figure 4A:
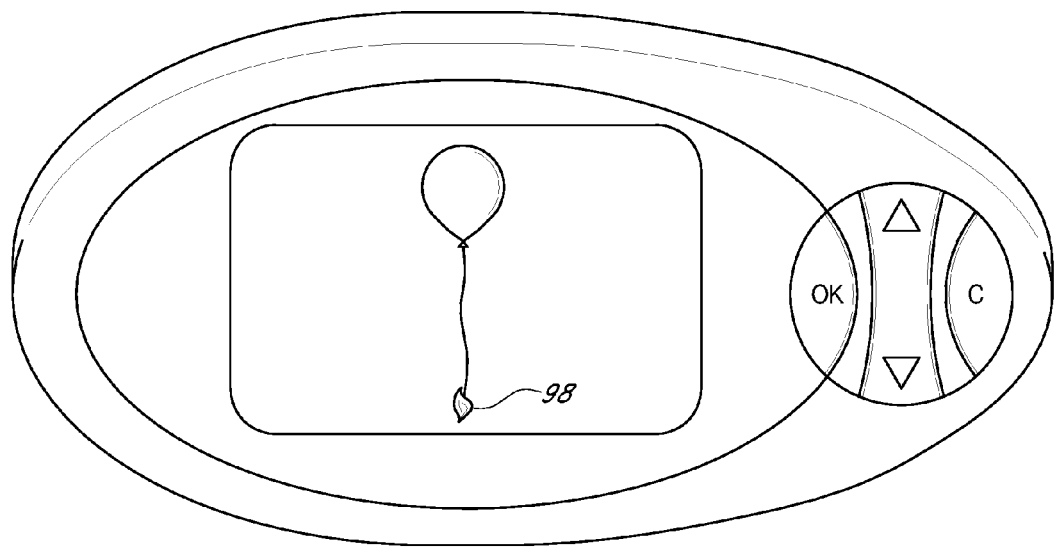
FIGS. 4A-4G are drawings illustrating an embodiment of displayed sensor data.
Figure 4B:
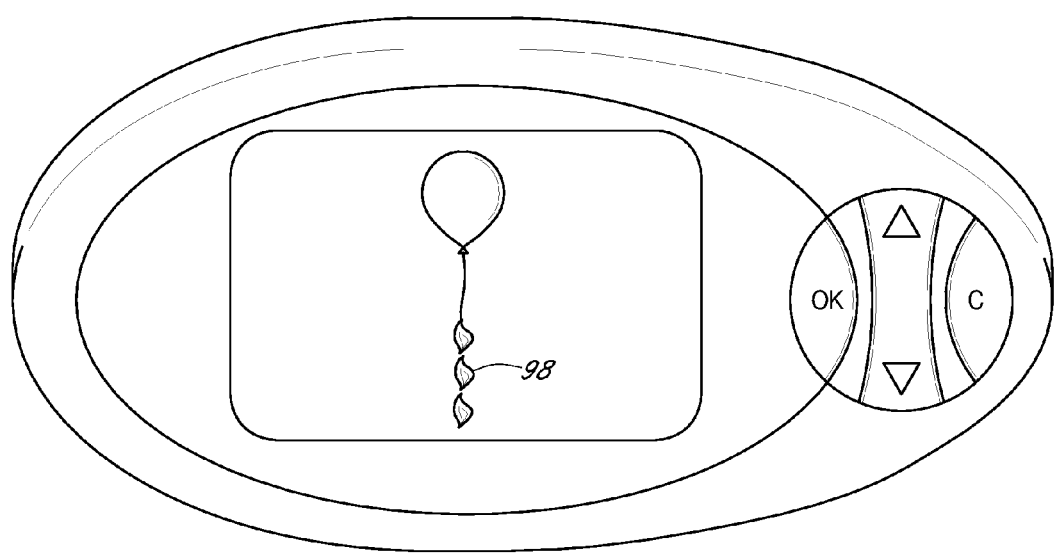
Figure 4C:
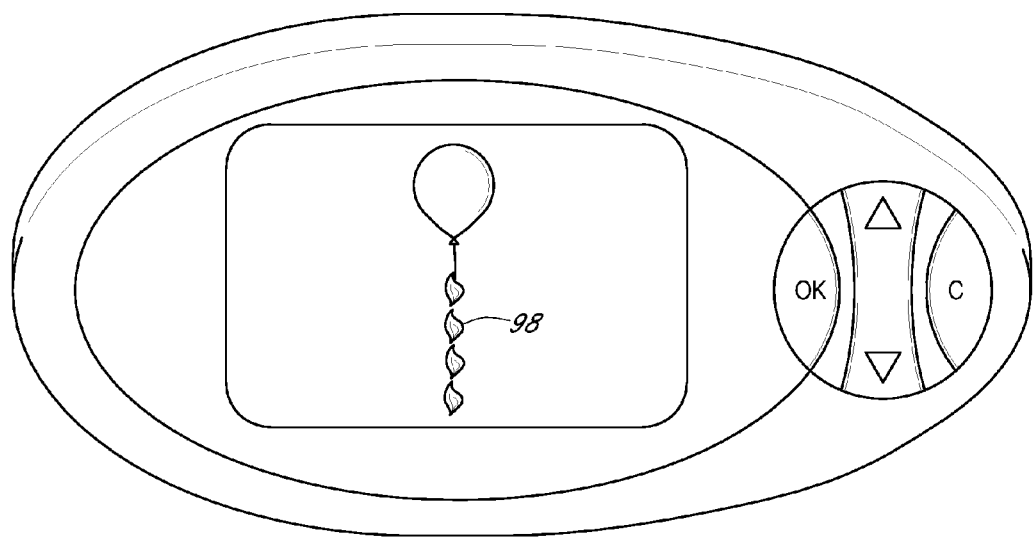
Figure 4D:
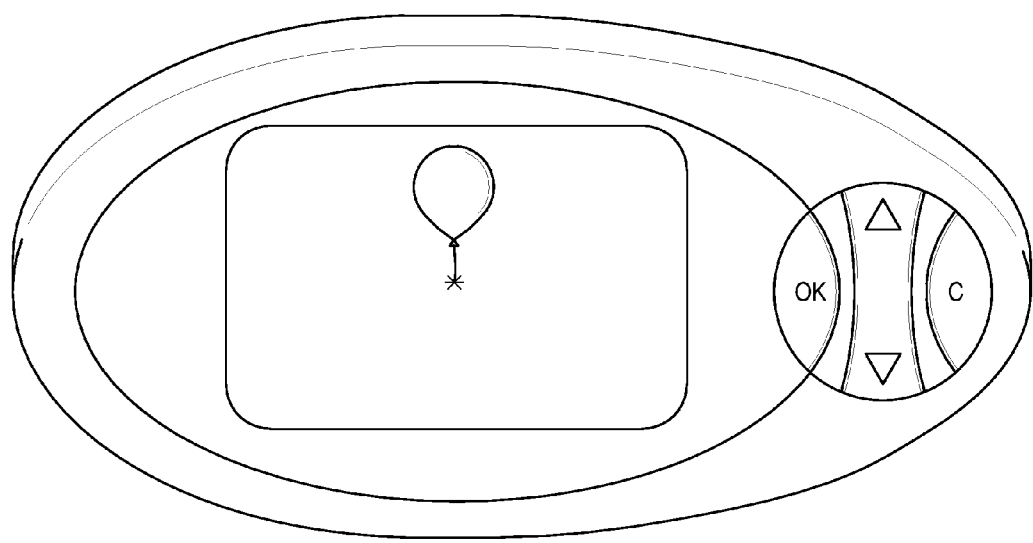
Figure 4E:
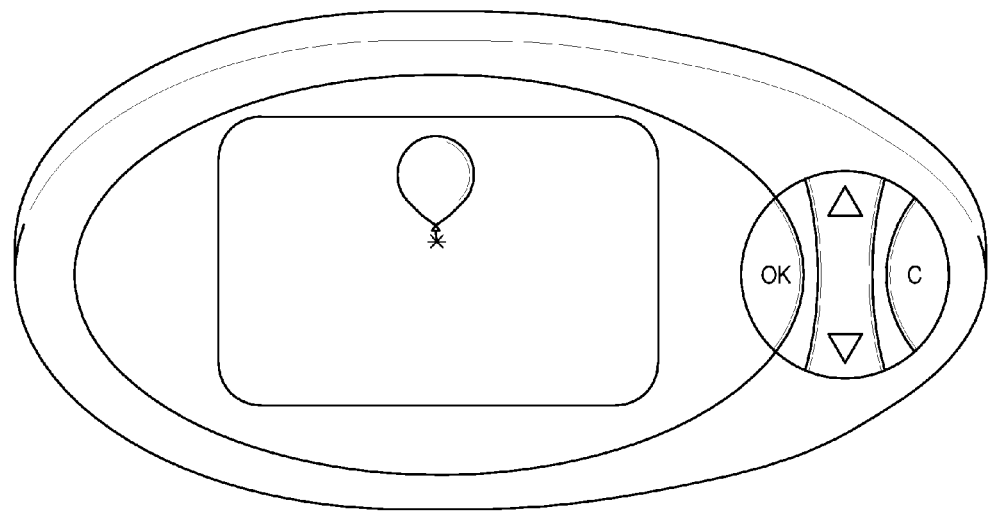
Figure 4F:
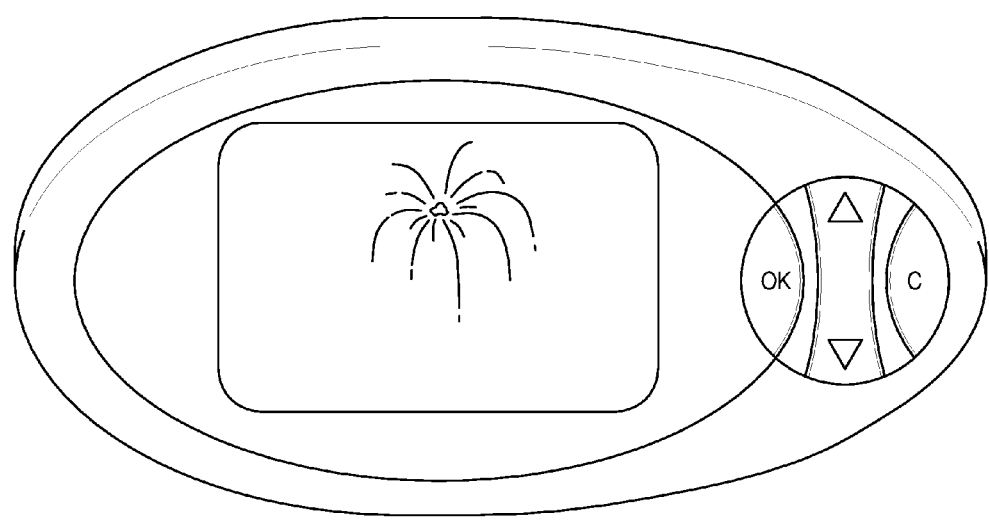
Figure 4G:
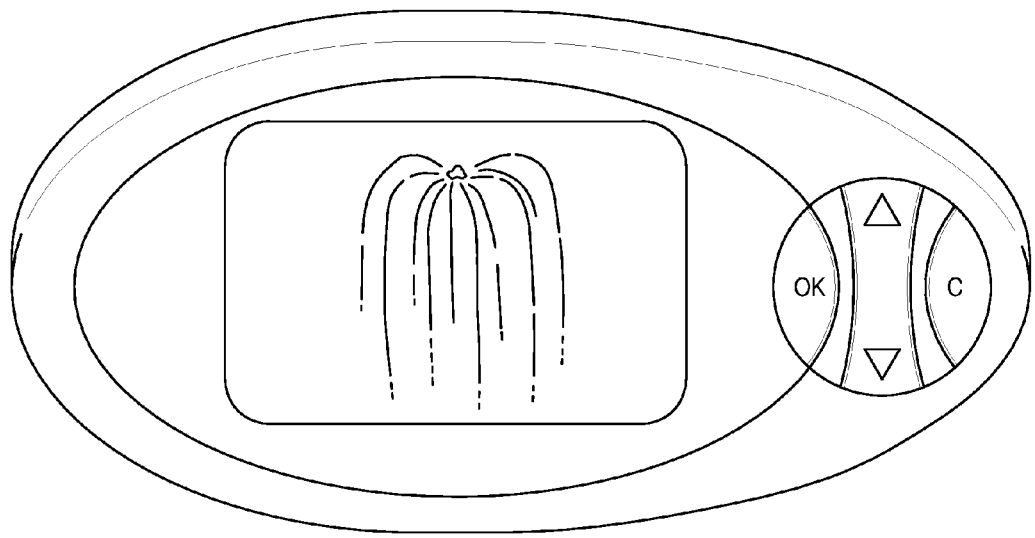

FIGS. 3E-3H are drawings representing other exemplary frames illustrating graphics representative of historical and current sensor data. In these embodiments the graphics 92 associated with historical sensor data trace paths of respective objects 94 moving toward respective targets 96. In some embodiments, once the object hits the target, such as by having the latest sensor data within a desired range, an animation is displayed. For example, in the embodiment of FIG. 3E, an animation showing a bowling ball knocking down the pins may be displayed. In the embodiment of FIG. 3F, the hitter may be shown hitting a home run. In the embodiment of FIG. 3G, the dog may be shown eating the treat. In the embodiment of FIG. 3H, the frog may be shown eating the fly. Depending on the embodiment, the games may be configured so that the targets 96 are reached at predetermined times of the day, such as just before lunch, dinner, and/or bedtime.

In addition, various embodiments can be configured to give different types of awards depending upon whether the historical and current data stay within one or more predefined ranges (e.g., 1, 2, 3, 4 or more different ranges). Each award can correspond to a different award value or range of values, so that a higher award can be given if a host achieves a higher award value and a lower award can be given if the host achieves a lower award value. For example, if the historical and current data stay within a first, narrow range for a predetermined amount of time, then a higher award is given than if the historical and current data exceeds the first, narrow range during one or more time periods, but never exceeds a second, broader range during the predetermined amount of time. To illustrate, this process can be used in an environment of a virtual baseball game provided on receiver 12. In this regard, should the historical and current data stay within a first range for a predetermined amount of time, then the highest award, such as a home run, is awarded; if the historical and current data exceed the first range, but does not exceed a second range for the predetermined amount of time, then the second highest award, such as a triple base hit, is awarded; if the historical and current data exceed the first and second ranges, but does not exceed a third range for the predetermined amount of time, then the third highest award, such as a double base hit, is awarded; if the historical and current data exceed the first, second and third ranges, but does not exceed a fourth range for the predetermined amount of time, then a fourth highest reward, such as a single base hit, is awarded; and if the historical and current data exceed the first, second, third and fourth ranges at one or more points in time during the predetermined amount of time, then the lowest reward, such as a strike, out, end of game or the like, will be given. The process can then repeat with a new predetermined amount of time and a score of the baseball game can be tallied based on the results. In this manner, a virtual baseball game can be played based on a host's glucose sensor data.

Moreover, in place of or in addition to the various ranges discussed above, a type of reward given (e.g., homerun, base hit or out) can be based wholly or partly on other criteria. For example, the type of reward given can depend on a duration and/or amplitude of the historical and current data exceeding one or more ranges before the historical and current data fall back within the range during the predetermined amount of time. To illustrate, a homerun can be awarded if the historical and current data never fall outside of a range during the predetermined time period, and a triple base hit can be awarded if the historical and current data fall outside of the range for less than a threshold duration and/or the amplitude of the sensor data exceeds the range by less than a threshold amplitude. Second and single base hits can similarly be awarded based on other thresholds not being exceeded. An "out" or "end of game" can be given if one or more (including all) thresholds are exceeded. In the event both the amplitude and duration thresholds are taken into account for awarding a type of award, various weighting measures can be applied to the amplitude and duration threshold exceeded for determining the type of reward given.

FIGS. 4A-4G are a series of drawings representing other exemplary frames illustrating an animation representative of historical and current sensor data. In the series of Figures, a number of flames 98 are shown, where each of the first three frames (FIGS. 4A-4C) illustrate a successively greater number of flames 98. Each flame 98 represents a good glucose level, for example, a day in the past 30 days when the glucose level stayed within a target range, or an amount of time of the current day when the rate of change in the glucose level was less than a threshold. If a sufficient number of flames 98 are generated, an animation follows, which shows a fuse being lit, and fireworks exploding (e.g., FIGS. 4D-4G).

Figure 5:
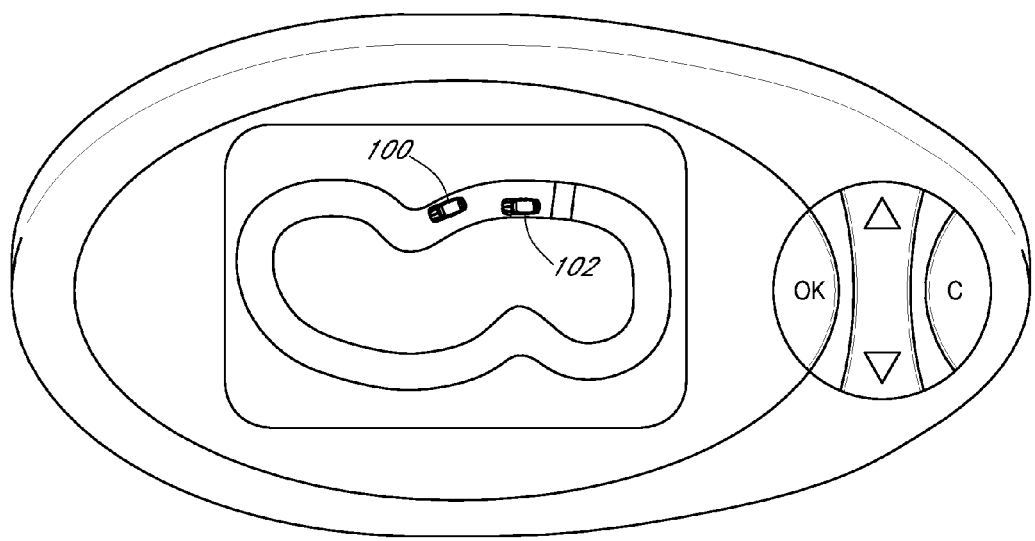
FIG. 5 is a drawing illustrating an animation graphically comparing two sets of sensor data.

FIG. 5 shows another exemplary frame illustrating graphics representative of historical and current sensor data. In this embodiment, the graphics are associated with at least two types of sensor data, such as data sets associated with a percentage of time within a target glucose range and percentage of time outside of the target glucose range. In this embodiment, two cars 100 and 102 are on a race track. Each car represents one of the data sets. Some aspect of each cars performance corresponds to the data of the associated data set. For example, the speed or the distance traveled for car 100 may represent a first data set—the percentage of time in target range, and the speed or distance traveled for car 102 may represent a second data set—percentage of time out of target range. Thus, the animation of FIG. 5 illustrates a graphical comparison of the two data sets. In some embodiments, the two data sets may be corresponding data (e.g., data from the same host) taken during two different time periods (e.g., the first data set may represent sensor data from a current week and the second data set may represent sensor data from a previous weeks). Accordingly, the animation may illustrate a graphical comparison of, for example, glucose control performance this week compared to last week.

Figure 6:
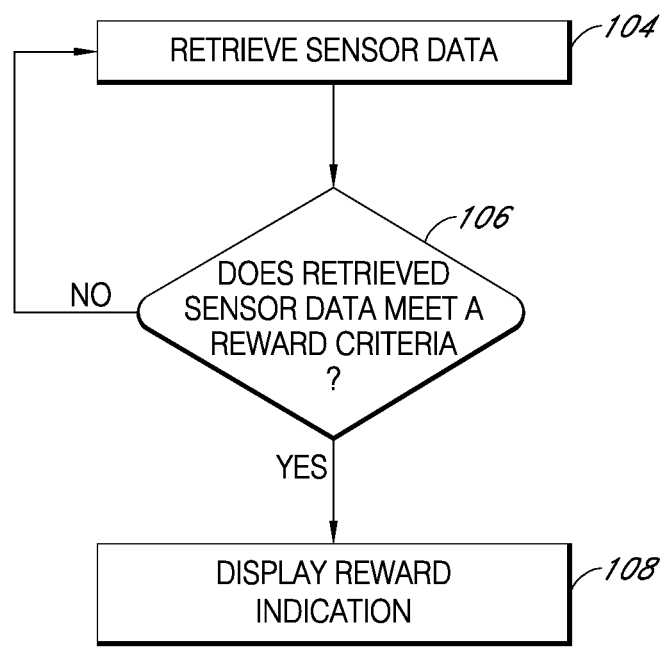
FIG. 6 is a flowchart that illustrates a process of displaying sensor data as a game where rewards are given.

FIG. 6 is a flowchart illustrating an embodiment of a method of displaying sensor data as a game where rewards are given. The process is used by, for example, a receiver, such as receiver 12 of FIG. 1. The process includes retrieving sensor data 104, determining whether the retrieved data meets a reward criteria 106, and displaying (or otherwise providing) a reward indication 108. In some embodiments, the process illustrated in FIG. 6 is initiated by a command generated in response to a request by a user. In some embodiments, the process is initiated by any interaction with the receiver which contributes toward meeting the reward criteria. In some embodiments, any interaction with the receiver contributes toward meeting the reward criteria.

The sensor data retrieved at block 104 includes at least one of current data and historical data. For example, the retrieved data may include the sensor data for the past 24 hours, or may include the sensor data for measurements taken between 12 pm and 6 pm. In some embodiments, the retrieved data may include transformed sensor data, such as calibrated and/or filtered blood glucose levels and/or one or more trend or rate of change indicators, for example.

The reward criteria to which the retrieved data is compared at block 106 may be dependent on the type of data retrieved. For example, if the retrieved data comprises sensor data for the past 24 hours, the reward criteria may be based on a minimum percentage of time for which the sensor data is within a target range. For example, the reward criteria may be set to 75%, and the retrieved data may indicate that the sensor data was within the target range 85% of the past 24 hours. In some embodiments, the reward criteria may be based on improvements in the sensor data. Accordingly, a comparison of the criteria with the retrieved data determines that the criteria for a reward has been met. If the reward criteria is not met, in some embodiments, the receiver displays an indication that the criteria is not met.

In one embodiment, points are awarded in response to certain actions by the host, such as receiving sensor data including a glucose level that is within an acceptable range. Thus, if sensor data is received every 5 minutes, for example, the host may receive more points every 5 minutes. The points may be incremented until they reach a reward threshold and then the receiver may initiate communication of a reward to the host and/or caretaker, for example. The reward threshold may be an incremental point level, e.g., every 5,000 points, and/or may be associated with reaching a high score (e.g., higher than previously reached by the host, possibly within a certain time period).

If the reward criteria is met, at block 108 the receiver displays an indication of a reward. The indication may include a series of frames forming an animation. In some embodiments, the indication includes a single frame. In some embodiments, the display depicts the retrieved data, the criteria, and the reward indication simultaneously. Other rewards include having the opportunity to select a new "skin" for the receiver (e.g., colors, icon designs, etc.), unlocking levels of a game, unlocking an avatar, receiving credits towards purchase of a product. In some embodiments, the reward indicator is transmitted to a caretaker indicating that the user has met the reward criteria. The reward indication may be transmitted, for example, to a mobile device of the caretaker via email or sms. In some embodiments, the reward indication is randomly or pseudo-randomly selected from a plurality of stored reward indications.

In some embodiments, analysis information for the retrieved data, such as the target range, and the reward criteria, such as the 75% time within range, are entered by the user. In some embodiments, access to the entry of the analysis information and the reward criteria is limited by a security device, such as a password. For example, a parent may enter a password to gain access to a data entry mode by which the parent enters reward criteria, e.g., 75% within a target range over a 24 hour period.

Figure 7A:
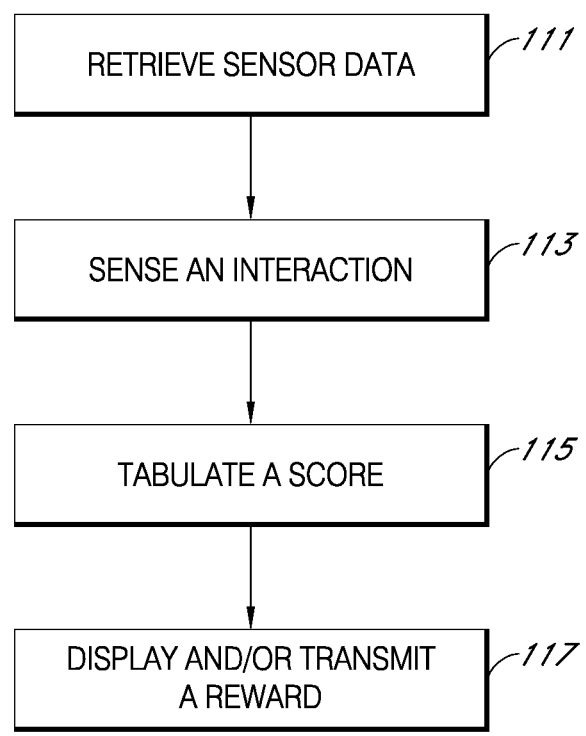
FIG. 7A is a flowchart that illustrates a process of generating rewards based on user interaction.
Figure 7B:
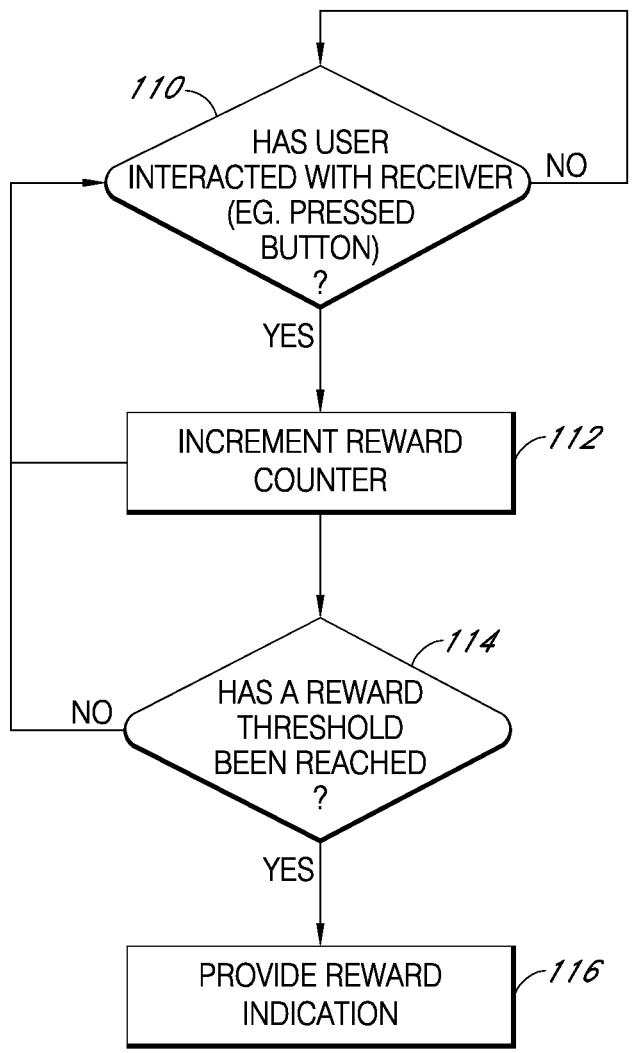
FIG. 7B is a flowchart that illustrates another process of generating rewards based on user interaction.

FIGS. 7A and 7B illustrate embodiments including systems and methods for providing rewards to a user to encourage interactions associated with a continuous glucose monitoring system. Some studies of pediatric diabetes have shown that as the child increases interactions with their receiver, hypoglycemic and hyperglycemic events are decreased. Much of this difference in glucose control may be due to the fact that users that are interested in being diligent in controlling glucose levels will interact with the receiver more according to this interest. However, this improvement in control can also be attained with less naturally diligent users by encouraging interactions of all kinds with the glucose monitoring system, even when those interactions are independent of the creation of or value of any sensor data. Encouraging a variety of different interactions with the system (in some embodiments all or substantially all interactions) will indirectly promote familiarity with the system operation, familiarity with typical user glucose levels, and familiarity with the effects user behavior has on their glucose levels. All these things will help the user control glucose levels better. Thus, by providing rewards to a child or other user with diabetes in response to many different types of interactions with their receiver or other portions of the monitoring system (e.g. pressing various buttons, changing display outputs, setting alarms, etc.), the frequency of hypoglycemic and/or hyperglycemic events may in turn be decreased.

In one such exemplary embodiment, the continuous glucose monitoring system includes a glucose sensor configured to provide real-time continuous glucose sensor data, a portable device comprising a user interface configured to receive user input and display the real time glucose sensor data responsive to user-interaction with the portable device and a processor module configured to tabulate a score based at least in part on user interactions with the user interface. While the exemplary embodiment may include a configuration wherein the processor module may be located within the portable display device, it should be understood that some or all of the processing and electronic circuitry associated therewith can be located local to the sensor, for example, within a transmitter body wired to the sensor. Additionally, some or all of the processing and electronic circuitry associated therewith can be located within hardware or software operably connected with the monitoring system, for example, through a download cable or through a wireless connection to a personal computer, mainframe computer, server, or the like.

Referring now to FIG. 7A, at block 111, the processor module is configured to retrieve the sensor data, either directly or indirectly through a wired or wireless connection with the sensor. As described in more detail elsewhere herein, the data can be transformed using a variety of algorithms to provide useful data to a user. Examples of useful data include not only real-time analyte values, but can also include trend information in the form of graphs or directional indicators, statistical data associated with a period of time, improvement in diabetes management or other metabolic control associated with an improvement with analyzed data from one time period to another time period, amount of time within a target range, and/or the like.

At block 113, a user interaction with the continuous glucose monitoring system is sensed or detected. In the exemplary embodiment of a portable display device, wherein the device is configured to receive sensor data from the glucose sensor, the device is configured to selectively display information associated with the sensor data and/or the sensor data in response to interactions from the user, which can be sensed by the device. However, other user interactions with the continuous glucose monitoring system can be sensed; for example, interactions associated with a remotely located device, such as a software program or internet site running on a computer system associated with the continuous glucose monitoring system, and these interactions can be provided to the portable display device, or any processing circuitry associated with the continuous glucose monitoring system that tabulates a score or increments a reward, as described in more detail elsewhere herein.

In some embodiments, the sensed interaction includes at least one of pressing a button, touching a screen of the receiver, activating another input device, selecting sensor data for viewing on the receiver, downloading data, inputting events, setting parameters, confirming sensor data, and the like. In some embodiments, the score may be based at least in part on receiving sensor data during a predetermined time period. In some of these embodiments, the system may sense an interaction with the system that comprises the attachment or continuous wearing of at least a portion of the glucose monitoring system for a predetermined amount of time. The attachment or placement of the receiver on the user may, for example, be detected by continuous or periodic reception of sensor data from an implanted sensor without significant interruption or periods of failed data reception. For example, wherein the monitoring system is configured for a particular sensor session time period (e.g., 3, 5, 7, 10 days, or the like), score or reward counters may be incremented based at least in part on a completion of a sensor session (e.g., 3-, 5-, 7- or 10-day sensor session), a plurality of sensor sessions (e.g., 1, 2, 3, 4, 5, 6, 7, or more sensor sessions), predetermined number of substantially consecutive sensor sessions, a predetermined time period (e.g., 1-, 3-, 5-, 7-, 10, 14-, 21-, 30-day, or more), or the like.

In some embodiments, the sensed interaction is any action that causes current sensor data to be displayed. For example, pressing a button, touching a screen, adjusting an alarm for increased sensitivity (e.g., more sensitive alarm thresholds). In some embodiments, the sensed interaction causes historical sensor data to be displayed, for example display of the 1, 3, 6, 9, 12, 24 hour trend screen(s) or the like. In some embodiments, the sensed interaction initiates or changes a display on the receiver. For example, pressing a button or touchscreen may awaken the device from a sleep mode and cause the device to display current sensor data. A button push may change the display from current data to historical data, or may change the display to one that contains a projected future glucose concentration. It may be noted here that the score increase or reward may be given in response to many different interactions regardless of the user's diligence in measuring glucose levels or success at maintaining them. Providing rewards based at least in part on such interactions, however, may lead to better success at glucose control in the future.

At block 115, the processor module is configured to tabulate a score, also referred to as incrementing a reward counter, associated with one or more user interactions, such as the user interactions described herein. In some embodiments, the processor module is configured to detect substantially all sensed interactions, where substantially all sensed interactions are input into the score tabulation or reward counter. In some embodiments, the processor module is configured to detect one or a plurality of predefined interactions, whereby the score or reward counter can be incremented. In some embodiments, the sensed interactions used to increment the score or reward counter are independent of the creation or value of any sensor data; for example, a user can be simply rewarded for interacting with the device regardless of any performance associated with their disease management.

In some cases, it is advantageous to include time based limitations on which interactions can cause the score or reward counter to be incremented. Thus, in some embodiments, the processor module is configured for sensing time periods between interactions, and incrementing the reward counter in response to a second interaction when the second interaction is sensed within a predetermined time period from a first interaction. For example, the score may be incremented only if interactions with the device are performed with a certain pre-defined frequency or frequency range. Excessive delay between interactions may result in reduced or no score increment. At the other end of the spectrum, to avoid having a user just mindlessly press buttons to achieve high scores, a limit on the amount of reward or score may be set for a given time period, for example, a user may achieve up to a predetermined number of points for up to a predetermined number of interactions in a predetermined time period. One of ordinary skill in the art can appreciate a variety of numerical and time-based limits that may be applied to encourage a reasonable or optimal interaction frequency.

As noted above, it is believed to be advantageous to increment scores/reward counters based on interactions that are not dependent on glucose measurements themselves. However, this does not mean that providing rewards for direct success in glucose management is not also worthwhile as part of a reward system. Thus, in some embodiments, the score may also be based at least in part on one or more sensor data values falling within a predetermined range. For example, when a predetermined number or average of a predetermined number of glucose values are within a target glycemic range over a period of time.

In some embodiments, the score is based at least in part on sensor data associated with a predetermined time period meeting one or more criteria. For example, criteria can include target range of analyte values, average and/or statistical measures of analyte information over a time period. Average and/or statistical measures can include area under the curve, MARD, ARD, A1c, and the like. Some additional examples include measures of, sustained outcomes of increased normoglycemia, decreased area under curve, decreased hypoglycemic episodes, decreased variability, and the like.

In some embodiments, the score is based at least in part on a change in one or more sensor data values within a predetermined time period immediately after an alarm is triggered. For example, when a hypoglycemic alarm is triggered, a score can be tabulated based on the amount of time before the user achieves normoglycemia (e.g., glucose within a predefined target range). For example, the increment or value of the score can be based on whether the user achieves normoglycemia within 10, 20, 30, 40, 50, 60, 90, 120 or more minutes.

In some embodiments, the score is based at least in part on sensor data associated with a first time period indicative of an improvement in glycemic control or diabetes management as compared to sensor data associated with a historical time period, including averages or statistical measures evaluated over a predetermined time period. For example, if a user decreases the amount of time spent in a hyperglycemic range during a week time period as compare to a previous week time period, a particular score or reward amount can be calculated or tabulated. It should be appreciated that numerous other statistical and/or analytical measures of analyte data can be used to compare between any definable time periods and provided with any number or scoring options associated therewith, as can be understood by one of ordinary skill in the art.

In some embodiments, the score is based at least in part on user interactions involving setting of or changing of receiver operation parameters. Some receiver operation parameters include alarm settings (e.g., analyte thresholds, rate of change thresholds, predictive alarm settings, type of output, display features, and the like). It should be noted that operational parameters can be also be set, displayed and/or applied in a portable device type receiver and/or any other device that receives and/or displays the sensor data, including, downloadable software, web-hosted databases, servers, and the like.

In some embodiments, the score is based at least in part on user interactions that cause downloading of data by a user from the receiver to another processing system, for example downloadable software, web-hosted databases, servers, and the like. In some embodiments, the score is based at least in part on whether or how the user sets or confirms alarm settings on the receiver; for example, when an alarm criteria is met, the receiver triggers an alarm, and the user acknowledges the alarm by pressing a button, touching the screen, or the like.

In some embodiments, the score is based at least in part on an evaluation of the sensor data to determine whether the user is maintaining good control, for example by tracking a running average of average glucose over time. Maintaining good control can include a variety of statistical and clinical evaluations of the data, wherein the determination of good control or improvement in a particular patient's diabetes can be user settable, physician settable, adaptable by an algorithm on the system, relative to a previous sensor session or time period, or the like.

In some embodiments, the score is based at least in part on user events, for example, when a user enters an event into the receiver and/or other systems associated with the system. Some examples of events include caloric intake, level of activity, health, and the like.

Whether tabulating a score, incrementing a reward counter, or the like, it should be appreciated by one of ordinary skill in the art that different criteria can be given different weighting and/or points. For example, wherein the goal of a physician is to simply encourage regular wear of the continuous glucose monitoring system, the system can be set with a heavy weight (e.g., highest scoring) for continuous sensor wear and/or user interaction as compared to achieving targets with regard to sensor data. Numerous scoring or incrementing methods can be implemented by the manufacturer, user settable (e.g., by a user or care giver), via downloadable software, via communication with an interne site and/or the like.

At block 117, the processor module is configured to display a reward indication (or score) on the receiver and/or transmit a reward indication (or score). A score can be a numerical value associated with a calculation with a variety of user interactions, however, other methods of scoring are possible. A reward indication, which can include a score and/or be based at least in part on a score, can provide a physical and/or conceptual reward, including but not limited to a numerical value, credit from the manufacturer, an "opt-in" to a social networking group or site, changing of a display on the receiver when the score reaches a predetermined reward threshold (e.g., transformation of character or display animation as a reward such as described above with reference to FIGS. 3-5), achieving new sounds (e.g., tones, downloading of tones, animation, etc), and the like.

The reward indication can be displayed on and/or transmitted to any component associated with the continuous glucose monitoring system, including, a user interface of a portable receiver, a text or email to a care giver's device linked to the user's system, downloadable software, internet site, and the like). Additionally, the score or reward indication can be configured to be displayed or transmitted continuously, at predetermined levels of achievement, at a predetermined reward threshold or value, at predetermined time periods or events, and the like.

In some embodiments, displaying and/or transmitting the reward includes transmitting a score and/or reward to an internet site, whereby users can connect with other users' and/or their physician to share or compete. It is believed that by interacting through social networking or data sharing, additional motivation can be achieved. Additionally, rewards can be used by a manufacturer to provide credits, new features, upgrades, accessories, and the like.

FIG. 7B is a flowchart that illustrates another exemplary process of generating rewards based on interactions of the host with the receiver. The method of FIG. 7B may be performed by a receiver, such as receiver 12 of FIG. 1. Depending on the embodiment, the method of FIG. 7B may include fewer or additional blocks and/or the blocks may be performed in an order than is different than illustrated.

In the embodiment of FIG. 7B, interactions with the receiver contribute towards meeting one or more reward criteria. The method of FIG. 7B includes determining that an interaction with the receiver has occurred 110, incrementing a reward counter 112, determining whether a reward threshold has been reached 114, and providing a reward indication 116.

At block 110 an interaction with the receiver is sensed. Depending on the embodiment, and as described above as well, the interaction may include pressing a button, touching the screen, or activating another input device on the receiver. Interactions may also include other actions taken by the user, such as viewing sensor data on an external device. In some embodiments, interaction includes downloading data, inputting events, setting parameters, confirming sensor data, and the like, as described in more detail elsewhere herein. In some embodiments, interaction is based on an amount of time the sensor is used, for example, over a predetermined time period.

At block 112 a reward counter is incremented in response to sensing of an interaction at block 110. In some embodiments, all interactions generate a same increment value. In some embodiments, some interactions have higher increment values than other interactions. For example, interacting with the receiver in order to view glucose level trend information may be associated with a higher increment value than interacting with the receiver in order to view a current glucose level. In one embodiment, increment values for the same or similar interaction may be, limited during a predetermined time period. For example, a child may be limited to receiving reward points only for a first 5 times that a particular button on the receiver is pressed within any 5 minute period. In some embodiments, increment values for various interactions are programmable.

In addition, a higher increment value award can be given if a first interaction is followed by a particular second interaction. The first interaction can be different from or the same as the second interaction. As an example, a higher increment value can be given if a user follows interacting with the receiver 12 in order to view glucose level trend (a first interaction) with exercise (a second interaction). In various embodiments, the receiver 12 receives or generates exercise data for determining whether the host has exercised from one or more external or internal devices, such as a GPS device, accelerometer and a heart rate sensor. Furthermore, a higher increment value can be awarded based on the level of exercise performed as determined from the exercise data.

At block 114 the value of the reward counter is compared to a reward threshold. If the comparison indicates that a reward has not been achieved, the method returns to block 110. However, if the comparison indicates that a reward has been achieved, the method moves to block 116, where a reward indication is provided to the host, a caretaker, a doctor, and/or other interested party. The reward indication may be similar to the reward indication of block 108 of FIG. 6.

FIG. 8A is a flowchart illustrating one embodiment of a method of interacting with a host via a tutorial. The method of FIG. 8A displaying tutorial data to the host, such as a series of glucose levels of an exemplary host, receiving input from the host of an action that should be taken in response to the provided exemplary glucose levels, and generating next glucose levels in response to the received input from the host. In this way, the tutorial may be used to educate the host as to how certain actions affect (or don't affect) the blood glucose levels. The tutorial data may be used to educate the user about expected consequences to various actions in various circumstances. The method may be performed by, for example, a receiver, such as receiver 12 of FIG. 1. Depending on the embodiment, the method of FIG. 8 may include fewer or additional blocks and/or the blocks may be performed in an order than is different than illustrated.

For example, a tutorial may display graphics representing glucose measurements that are increasing. The user may select exercise as a response. The tutorial then calculates simulated glucose values based at least in part on the response. In this example, the tutorial helps the user become more familiar with expected results of performing the various actions.

FIG. 8B illustrates three series 810A, 810B, 810C, of frames that may be displayed on a receiver as part of an interactive tutorial. Each of the frame series 810 has three frames, including a first frame 121 that corresponds with block 120 of FIG. 8A wherein tutorial data is displayed to the host, a second frame 123 that correspond with block 122 of FIG. 8A wherein input of a simulated action is received from the host, and a third frame 127 that correspond with block 126 of FIG. 8A including graphics indicating simulated glucose measurements that are responsive to the simulated action received from the host.

Beginning in block 118, the receiver determines tutorial data. The tutorial data may be based at least in part on actual measurements from a glucose monitor and/or other sensor, such as episodic SMBG. In some embodiments, the measurements were taken while monitoring the current host and stored in a memory. In some embodiments, the memory has data from one or more other users. The memory data may additionally contain synthesized data, which is not the result of measurements, but is generated by a method or using a synthesis algorithm. The memory may contain data representing various glucose excursion scenarios, such as blood glucose levels increasing towards hyperglycemia and decreasing towards hypoglycemia.

In one embodiment, patterns in the tutorial data are identified and a list of potential causes, allowing user, doctor/HCP, algorithm or remote analysis to determine most likely causes, are generated and displayed as a list of potential solutions or responses. With the potential solutions/responses, the user, doctor/HCP, algorithm or remote analysis can then determine the most likely actions or responses to recommend. In one embodiment, the response impact may be estimated by the sensor electronics and/or documented, e.g. whether the user/caretaker followed the advice, and if not what actions were taken. In one embodiment, similar methods may be used in data management software or any remote analysis done whether by algorithm or remote HCP or clinical personnel or other trained to interpret data.

At block 120, the tutorial data is displayed. The tutorial data may be displayed as a series of frames displaying a game, an animation, or a cartoon. For example, a series of blood glucose levels may be displayed as graphics similar to those of any of FIGS. 3A-3H. In other embodiments, the tutorial data may be displayed in the form of textual data or as one or more graphs. As noted above, frames 121 of FIG. 8B illustrates exemplary displayed tutorial data.

Next, in block 122, the receiver receives an indication of an input from the host. The input indicates an action to be taken in response to the currently displayed tutorial data. For example, the action can be any of eating food, eating a glucose tablet, exercising, injecting insulin, responding to stress or injury, contacting someone for help, such as a teacher, a parent, or a medical professional, and/or taking no action. As noted above, frames 123 of FIG. 8B illustrate selected actions 125 displayed alongside the glucose data so as to indicate the relative timing of the actions 125 and the glucose data.

At block 124, the receiver simulates a response to the action indicated by the user. For example, based on the glucose levels, trends in the glucose levels, and/or the action indicated by the user, a processor in the receiver may generate a simulated response to the action based on a simulation algorithm. In one embodiment, a trend in the tutorial data may not change immediately after the host indicates that an action should be taken. For example, if the host indicates an action of eating food, the tutorial data may not indicate any changes in the current trend of the blood glucose levels for 30 minutes (or some other time period) representative of a time period that is required to digest the food and increase the blood sugar levels of the exemplary host. In one embodiment, the simulated responses may be compared to sensor data that was actually measured/seen, and the different in the simulated responses and the actual responses may be utilized in by the algorithm for additional user customization and response knowledge.

At block 126, the simulated response to the action is displayed. As noted above, frames 127 of FIG. 8B illustrate simulated responses displayed along with the tutorial data and the actions 125. In some embodiments, the simulated response is displayed along with the data representing measurements prior to the action. In some embodiments, the action take is represented with an icon in the display. In some embodiments, an animation is generated indicating the simulated response. In some embodiments, a reward indication is displayed if reward criteria are met. In some embodiments, simulated responses for one or more alternate actions may be generated and displayed, for example, in response to an input indicating a request for such a display. In some embodiments, a simulated response of an alternate action is generated and displayed if the action indicated by the user is not optimal.

In one embodiment, the method repeats blocks 120-126 as more simulated actions are received from the host and more simulated blood glucose levels responsive to the actions are generated by the receiver. In this way, the host is able to simulate an extended time period of activities (e.g., from morning until night) in a very short time frame (e.g., in 1-15 minutes, for example) while learning how certain actions affect blood glucose levels. In one embodiment, the graphics used for the tutorial are similar/same as used for the actual sensor data of the host, e.g., one or more of the games illustrated in FIGS. 3A-3H or the like.

Figure 9A:
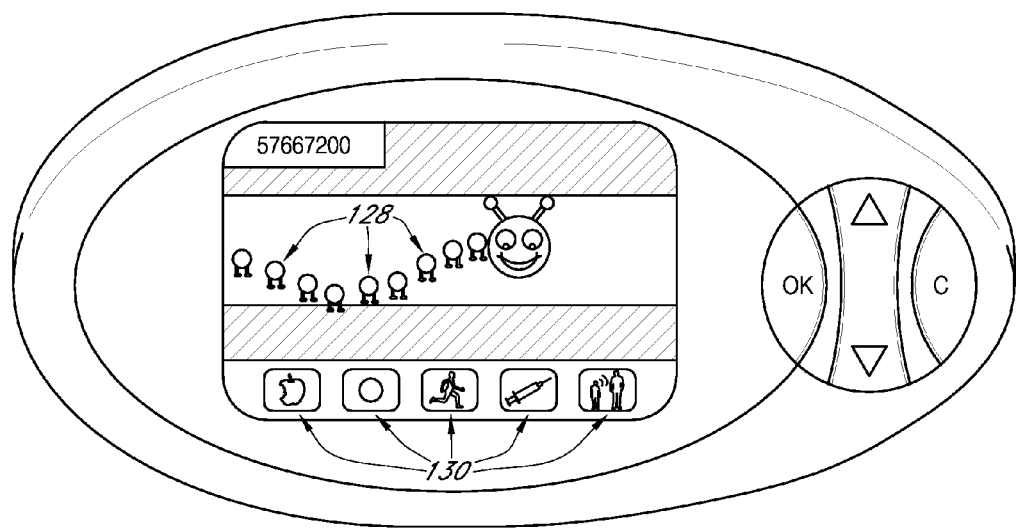
FIGS. 9A and 9B are drawings illustrating embodiments of displayed tutorial data.
Figure 9B:
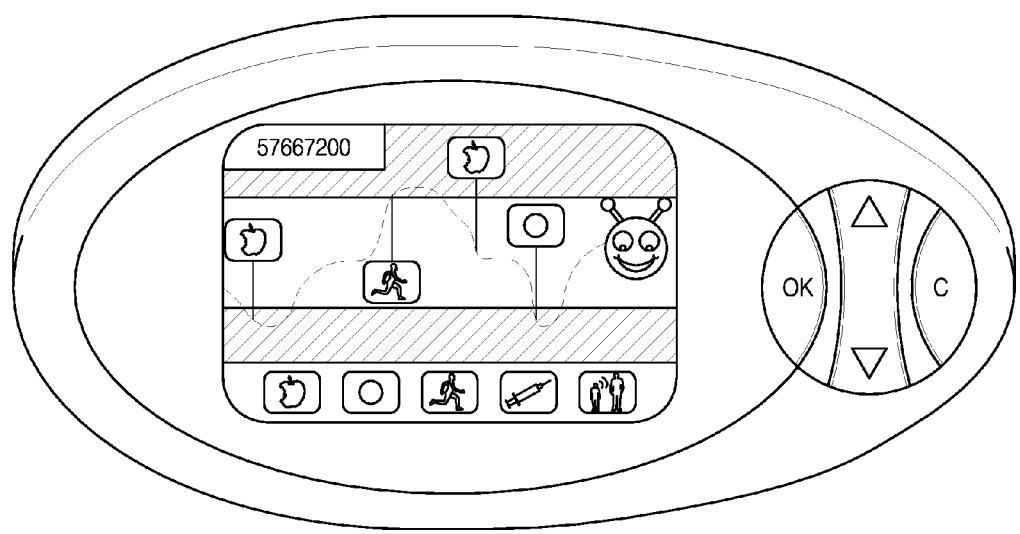

FIGS. 9A and 9B are drawings illustrating embodiments of displayed tutorial data. FIG. 9A shows tutorial data 128 representing a selected glucose scenario. Icons 130 represent eating food, eating a glucose tablet, exercising, injecting insulin, or contacting someone for help, respectively. FIG. 9B shows tutorial data with actions and results of the actions. In some embodiments, the actions are real actions taken by a user from whom measurements were taken and are included in the tutorial data. In some embodiments, at least some of the actions are actions selected within a tutorial, and the measurements shown after the actions are simulated responses to the selected actions. In some embodiments, icons such as icons 130 are used outside of a tutorial to graphically indicate actions taken by the user.

Systems and methods can also be configured to provide a diabetes management game based on simulated or sample data. These games can be run and played on a computer system such as a PC, a PDA, a mobile phone, or the receiver 12 described above, for example. One mode can be configured to cause a user to compete against the computer system, wherein the computer system makes decisions (e.g., insulin dosing decisions) based on standard bolus wizards that take into account single point glucose sensor data (e.g., from a meter or significantly time spaced sensor data by at least about 4 hours) in one embodiment or continuous glucose sensor data (e.g., from an implantable sensor) in another embodiment. Preferably, the goal of this game is for the user to achieve a good score or beat the computer system. In one embodiment, the largest contributor to the score is based on exposure to glucose; in one embodiment, it could be an A1c score derived from the area under the curve over time. Deductions from the score can occur if a player has a severe hypoglycemia episode. Low variability of glucose concentration can amplify the score. The game can be designed to be repeatedly played by the user. In this exemplary embodiment, the game does not provide help or assistance or any advice about actions to take, but the game requires the user to read only the glucose information provided by an actual continuous glucose sensor session (e.g., glucose value, trend arrow, and/or graphical time display) and make insulin dosing decisions.

In one example, the game begins with simulated and/or sample data consistent with an "out of control" patient level (e.g., high glucose variability and/or high A1c) and sequentially move toward simulated and/or sample data consistent with a "well controlled" patient level (e.g., low glucose variability and/or low A1c) as the user successfully achieves tighter glucose control (e.g., reduced exposure to glucose). For example, a defined series of levels with increasing difficulty can be provided. All players may start with an A1c of 11 or higher. Corresponding high and low settings can be 120 and 300, for example. The user successfully completing this level can mean that the user has achieved an improved A1e of, for example, 10 or 10.5, and the game gets progressively more difficult as the A1c gets lower, and the high and low limits narrow.

For example, the screen moves along at about 1 hour every few seconds and at periodic times it freezes and states a scenario (e.g., "you are about to stop at fast food restaurant for a specified meal deal. How much insulin should you take?") The user enters their estimation for insulin dosing, while the computer enters its estimation for insulin dosing based on the bolus wizard value. At the end of a prescribed period of time, the player either loses or wins against the computer. Advantageously, the user is motivated to play again and again until they beat the computer and improved the glycemic control of the simulated or sample data is revealed. In embodiments wherein the bolus wizard is based on single point glucose sensor data, it is believed that the usefulness of continuous glucose sensor data can easily be exemplified. In embodiments wherein the bolus wizard is based on continuous glucose sensor data, the simplicity and ease of use of graphical and/or trend information associated with continuous glucose sensor data can be illustrated.

In another mode, the system can be configured to cause the user to play against a physician. In this mode, the system is configured to display a retrospective data set from a sensor session (e.g., 3.5 or 7 days of sample data) to the patient. The user is not given physician information, but instead makes insulin dosing decisions at specified events and/or time points in the data set. The computer system is programmed with physicians' instructions (from a real or sample physician). The goal of this game is to beat the physician. Advantageously, this mode raises awareness of the difficulty of analyzing data sets retrospectively, and points to the power of real time continuous glucose sensor data.

In yet another mode, the system can be configured to allow two or more users to compete. In this mode, the same simulated and sample data (real-time or retrospective) is provided to multiple users (e.g., user vs. doctor, users online, etc).

Figure 10:
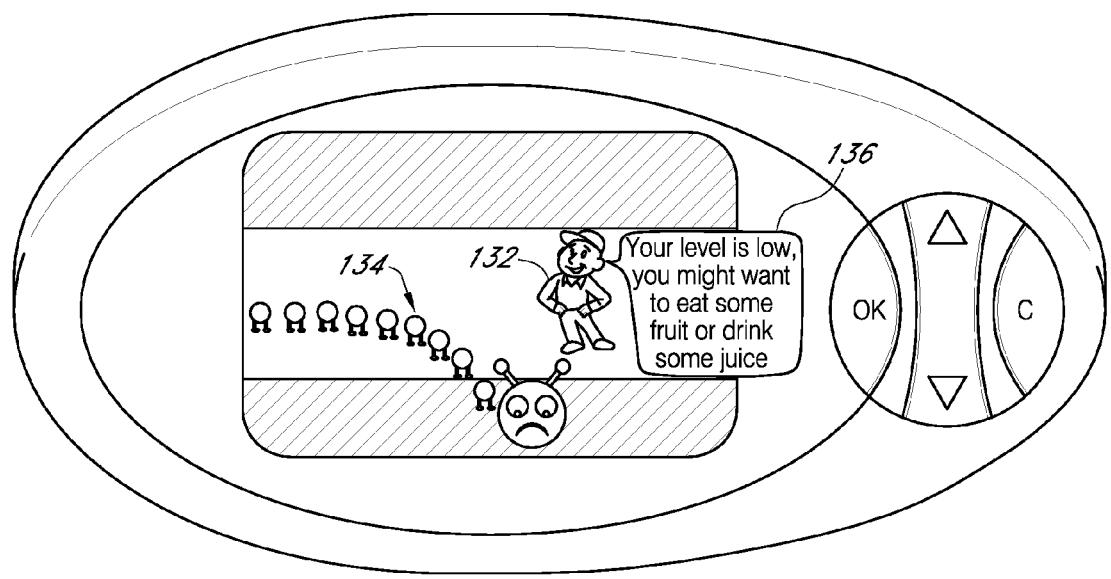
FIG. 10 is a drawing illustrating an embodiment of displaying data with a graphical character.

FIG. 10 is a drawing illustrating an embodiment of presenting information, such as sensor data or help information, in conjunction with an avatar or other graphical character. In this embodiment, a graphical character 132, such as a character that may be selected by a pediatric host (e.g., as a reward for maintaining their blood glucose level within a predetermined range over a certain time period) is displayed with sensor data 134, however, in some embodiments a graphical character is displayed without sensor data. In this embodiment, the graphical character 132 is displayed with a message 136, however, in some embodiments a graphical character is displayed without a message.

The graphical character 132 may be, for example, any of a person, a child, an imaginary creature, an avatar, an animal, or the like. In some embodiments, the graphical character 132 is a character used with other media, such as in television or movies. In some embodiments, the graphical character 132 is displayed as having supernatural abilities. The graphical character 132 may include one or more characters. In some embodiments, two or more characters are displayed as interacting with one another. In some embodiments, the graphical character 132 is selected through an input to the receiver. The graphical character 132 may include a portion or all of an uploaded pictures, such as pictures of family members, children, bucket list, etc. In some embodiments, the graphical character 132 is selected randomly or pseudorandomly from a group of selectable characters.

In the embodiment of FIG. 10, the graphical character 132 provides a message 136. The message 136 contains a therapeutic suggestion and/or motivational message in response to the sensor data 134. Other messages in response to the sensor data 134 may be used. For example, messages may include any of encouragement, congratulations, and warnings in response to the sensor data 134. In some embodiments, the message is not in response to sensor data. For example, the message may ask for input, such as requesting the user to indicate if the user has eaten lunch. The message may give a reminder to perform an action, such as to request the receiver to display sensor data from the past week. In some embodiments, the message may not be related to glucose monitoring. For example, the message may be a joke, or display the current time of day. Messages may be displayed on a display device of the receiver, may be pictorial or graphical, and/or spoken (e.g., in the voice of the character) using a speaker of the receiver.

In some embodiments, a character is displayed in response to an input by the user, such as the push of a button. In some embodiments, the character is displayed in response to another event, such as the sensor data having a specified characteristic, such as being above or below a threshold. The character may also be displayed in response to a time. The time may be programmed, or may be a random or pseudorandom time. In some embodiments, the character is used to display the sensor data, such as the centipede 134 of FIG. 10.

In some embodiments, a receiver (such as receiver 12) is configured to interface with a network to upload and/or download data. For example, using the receiver 12, the user may upload game scores, sensor data, and/or tutorial scenarios. In some embodiments, using the receiver 12, the user can download data representing games, graphics (such as graphics 70 and 72 of FIGS. 3A and 3B and graphic 82 of FIG. 3C), target graphics (such as target graphic 78 of FIG. 3B), animations (such as that shown in FIGS. 4A-4H and 5), rewards, backgrounds, sensor data, tutorial data, icons (such as icons 130 of FIGS. 9A and 9B), graphical characters (such as graphical character 132 of FIG. 10), and messages (such as message 136 of FIG. 10). The downloaded data, may, for example, be accessible only as a reward. For example, a reward may be achieved for glycemic control, where the reward allows the user or caregiver, for example, to access a network database and download a new avatar. In some embodiments, parents, doctors, and/or other caretakers of patients with diabetes may make recommendations that are provided to a particular host (or a group of hosts) in response to particular alerts. For example, the doctor of a particular pediatric patient may customize textual, graphical, audible, and/or other information that may be provided to the particular patient in view of the doctors knowledge of the patient needs, tolerances, etc.

In general, any of the above methods of data input and output can be combined, modified, selectively viewed, selectively applied, or otherwise altered without departing from the scope of the present invention. The various tasks performed in connection with processes (i.e. methods) described herein may be implemented by software, hardware, firmware, a computer-readable medium storing computer executable instructions for performing the process, or any combination thereof. It should be appreciated that the processes described herein may include any number of additional or alternative tasks. The tasks described and illustrated in the figures need not be performed in the described and illustrated order, and the processes may be incorporated into a more comprehensive procedure or process having additional functionality not described in detail herein. Moreover, the descriptions of the processes may refer to elements mentioned above in connection with FIG. 1, but it is understood that other devices and systems may be used to implement aspects of the processes.

For example, methods and devices that can be suitable for use in conjunction with aspects of the embodiments described herein are disclosed in U.S. applications including U.S. application Ser. No. 11/007,920 filed Dec. 8, 2004 and entitled, "SIGNAL PROCESSING FOR CONTINUOUS ANALYTE SENSOR"; U.S. application Ser. No. 10/695,636 filed Oct. 28, 2003 and entitled, "SILICONE COMPOSITION FOR BIOCOMPATIBLE MEMBRANE"; U.S. application Ser. No. 10/633,367 filed Aug. 1, 2003 entitled, "SYSTEM AND METHODS FOR PROCESSING ANALYTE SENSOR DATA"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE;" U.S. Pat. No. 6,931,327 issued Aug. 16, 2005 and entitled, "SYSTEMS AND METHODS FOR REPLACING SIGNAL ARTIFACTS IN A GLUCOSE SENSOR DATA STREAM"; U.S. Pat. No. 7,134,999 issued Nov. 14, 2006 and entitled, "OPTIMIZED SENSOR GEOMETRY FOR AN IMPLANTABLE GLUCOSE SENSOR"; U.S. Pat. No. 7,192,450 issued Mar. 20, 2007 and entitled, "POROUS MEMBRANES FOR USE WITH IMPLANTABLE DEVICES"; U.S. Pat. No. 6,702,857 issued Mar. 9, 2004 and entitled "MEMBRANE FOR USE WITH IMPLANTABLE DEVICES"; U.S. Pat. No. 6,741,877 issued May 25, 2004 and entitled "DEVICE AND METHOD FOR DETERMINING ANALYTE LEVELS"; U.S. Pat. No. 6,558,321 issued May 6, 2003 and entitled "SYSTEMS AND METHODS FOR REMOTE MONITORING AND MODULATION OF MEDICAL DEVICES"; and U.S. Pat. No. 6,862,465 issued Mar. 1, 2005 and entitled "DEVICE AND METHOD FOR DETERMINING ANALYTE LEVELS." All of the above patents and patent applications are incorporated in their entirety herein by reference.

The above description provides several methods and materials of the invention. This invention is susceptible to modifications in the methods and materials, as well as alterations in the fabrication methods and equipment. Such modifications will become apparent to those skilled in the art from a consideration of this application or practice of the invention provided herein. Consequently, it is not intended that this invention be limited, to the specific embodiments provided herein, but that it cover all modifications and alternatives coming within the true scope and spirit of the invention as embodied in the attached claims. All patents, applications, and other references cited herein are hereby incorporated by reference in their entirety.

All numbers expressing quantities are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

What is claimed is:

1. A method of rewarding a patient using a continuous glucose monitoring system to encourage taking corrective action, the method comprising:
    automatically generating sensor data using a continuous glucose sensor of the continuous glucose monitoring system while the continuous glucose sensor is continuously worn by a patient, the sensor data indicative of glucose concentration values of the patient over time;
    processing, using processor circuitry, the sensor data, wherein the processor circuitry is operably connected to the continuous glucose sensor;
    triggering, using the processor circuitry, an alarm responsive to the processing;
    initiating a timer responsive to the triggered alarm;
    modifying, using the processor circuitry, an animated character displayed on a user interface when the processor circuitry determines that one or more glucose concentration values as indicated by the sensor data satisfies a threshold level and the timer indicates a time less than a predetermined amount of time has expired from the alarm being triggered, thereby rewarding the patient based on corrective action taken by the patient.

2. The method of claim 1, further comprising generating the sensor data using the continuous glucose sensor while at least a portion of the continuous glucose sensor is continuously implanted transcutaneously in the patient, wherein the sensor data comprises a plurality of sensor data points, each sensor data point indicative of a glucose concentration of the patient.

3. The method of claim 1, wherein modifying the animated character comprises one or both of changing an expression of the animated character and changing a position of the animated character on the user interface.

4. A method of rewarding a patient using a continuous glucose monitoring system to encourage taking corrective action, the method comprising:
    automatically generating sensor data using a continuous glucose sensor while the continuous glucose sensor is continuously worn by a patient, the sensor data indicative of glucose concentration values of the patient over time;
    processing, using a processor circuitry, wherein the processor circuitry is located within or operably connected to the continuous glucose monitoring system, the sensor data;
    triggering, using the processor circuitry, an alarm responsive to the processing;
    modifying an animated character displayed on a user interface when one or more glucose concentration values as indicated by the sensor data satisfies a threshold level within a predetermined time period from the alarm being triggered, thereby rewarding the patient, wherein the predetermined time period is a time period used to evaluate how rapidly and effectively the patient responds to the alarm and rewards the patient if the one or more glucose concentration values satisfy the threshold level within the predetermined time period.

* * * * *

UNITED STATES PATENT AND TRADEMARK OFFICE
CERTIFICATE OF CORRECTION

PATENT NO. : 9,446,194 B2
APPLICATION NO. : 12/748069
DATED : September 20, 2016
INVENTOR(S) : Apurv Ullas Kamath It is certified that error appears in the above-identified patent and that said Letters Patent is hereby corrected as shown below:

On the Title Page

In Column 1 (page 6, item (56)) at Line 12, Under Other Publications, change "Senso" to --Sensor--.

In Column 2 (page 6, item (56)) at Line 10, Under Other Publications, change "basedon" to --based--.

In Column 2 (page 6, item (56)) at Line 41, Under Other Publications, change "reliablity" to --reliability--.

In Column 2 (page 6, item (56)) at Line 55, Under Other Publications, change "Enzymlology," to --Enzymology,--.

In Column 2 (page 6, item (56)) at Line 66, Under Other Publications, change "systme" to --system--.

In Column 1 (page 7, item (56)) at Line 1, Under Other Publications, change "artifical" to --artificial--.

In Column 1 (page 7, item (56)) at Line 24, Under Other Publications, change "your" to --you--.

In Column 1 (page 7, item (56)) at Line 38, Under Other Publications, change "dynamcs" to --dynamics--.

In Column 1 (page 7, item (56)) at Line 41, Under Other Publications, change "glocuse" to --glucose--.

In Column 1 (page 7, item (56)) at Line 42, Under Other Publications, change "Diabetese" to --Diabetes--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,446,194 B2

In Column 2 (page 7, item (56)) at Line 8, Under Other Publications, change "Diabetese" to --Diabetes--.

In Column 2 (page 7, item (56)) at Line 30, Under Other Publications, change "inactiviation" to --inactivation--.

In Column 2 (page 7, item (56)) at Line 44, Under Other Publications, change "patents" to --patients--.

In Column 2 (page 8, item (56)) at Line 33, Under Other Publications, change "activitiy," to --activity,--.

In Column 2 (page 8, item (56)) at Line 54, Under Other Publications, change "Beioelectronics," to --Bioelectronics,--.

In Column 2 (page 8, item (56)) at Line 55, Under Other Publications, change "glocuse" to --glucose--.

In Column 2 (page 8, item (56)) at Line 71, Under Other Publications, change "glucose-iunsulin interaaction in tyhpe" to --glucose-insulin interaction in type--.

In Column 1 (page 9, item (56)) at Line 17, Under Other Publications, change "Electronanalysis" to --Electroanalysis--.

In Column 1 (page 9, item (56)) at Line 61, Under Other Publications, change "amperometeric" to --amperometric--.

In Column 2 (page 9, item (56)) at Line 50, Under Other Publications, change "termistor" to --thermistor--.

In Column 2 (page 9, item (56)) at Line 51, Under Other Publications, change "metobolites," to --metabolites,--.

In Column 2 (page 9, item (56)) at Line 61, Under Other Publications, change "Apllied" to --Applied--.

In Column 2 (page 10, item (56)) at Line 25, Under Other Publications, change "Subcutaenous" to --Subcutaneous--.

In Column 2 (page 10, item (56)) at Line 39, Under Other Publications, change "assitance" to --assistance--.

In Column 1 (page 11, item (56)) at Line 23, Under Other Publications, change "pancrease" to

CERTIFICATE OF CORRECTION (continued)
U.S. Pat. No. 9,446,194 B2

--pancreas--.

In Column 2 (page 11, item (56)) at Line 11, Under Other Publications, change "Membrance" to --Membrane--.

In Column 2 (page 11, item (56)) at Line 46, Under Other Publications, change "Deabetes" to --Diabetes--.

In Column 1 (page 12, item (56)) at Line 8, Under Other Publications, change "Tranducers" to --Transducers--.

In the Specification

In Column 3 at Line 8, Change "andrenostenedione;" to --androstenedione;--.

In Column 3 at Line 24, Change "diptheria" to --diphtheria--.

In Column 3 at Line 31, Change "perioxidase;" to --peroxidase;--.

In Column 3 at Line 44, Change "duodenalisa," to --duodenalis,--.

In Column 3 at Line 52, Change "Trepenoma pallidium," to --Treponema pallidum,--.

In Column 3 at Line 53, Change "stomatis" to --stomatitis--.

In Column 4 at Lines 6-7 (approx.), Change "barbituates," to --barbiturates,--.